(12) United States Patent
Mukaibara et al.

(10) Patent No.: US 9,885,990 B2
(45) Date of Patent: Feb. 6, 2018

(54) IMAGE FORMING APPARATUS AND DETECTION APPARATUS FOR DETECTING POSITION OR DENSITY INFORMATION OF DETECTION IMAGE

(71) Applicant: CANON KABUSHIKI KAISHA, Tokyo (JP)

(72) Inventors: Takuya Mukaibara, Susono (JP); Hidetoshi Hanamoto, Mishima (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 14/441,977

(22) PCT Filed: Nov. 19, 2013

(86) PCT No.: PCT/JP2013/081575
§ 371 (c)(1),
(2) Date: May 11, 2015

(87) PCT Pub. No.: WO2014/097824
PCT Pub. Date: Jun. 26, 2014

(65) Prior Publication Data
US 2015/0293488 A1 Oct. 15, 2015

(30) Foreign Application Priority Data

Dec. 19, 2012 (JP) ................................. 2012-277442
Dec. 19, 2012 (JP) ................................. 2012-277443

(51) Int. Cl.
*G03G 15/00* (2006.01)
*G06K 15/02* (2006.01)
*G01N 21/55* (2014.01)

(52) U.S. Cl.
CPC ..... *G03G 15/5062* (2013.01); *G03G 15/5058* (2013.01); *G01N 21/55* (2013.01);
(Continued)

(58) Field of Classification Search
CPC ........... G03G 15/5062; G03G 15/5058; G03G 2215/0161; G03G 2215/0164; G06K 15/1878; G01N 21/55
See application file for complete search history.

(56) References Cited

U.S. PATENT DOCUMENTS 7,986,907 B2   7/2011   Miyadera
8,331,813 B2   12/2012  Ozeki
(Continued)

FOREIGN PATENT DOCUMENTS

JP   03-209281 A   9/1991
JP   09-247452 A   9/1997
(Continued)

OTHER PUBLICATIONS

Shinji Hosoya Takuya Mukaibara Kenichi Fujii, U.S. Appl. No. 14/441,972, filed May 11, 2015.
(Continued)

*Primary Examiner* — Joseph S Wong
(74) *Attorney, Agent, or Firm* — Fitzpatrick, Cella, Harper & Scinto

(57) ABSTRACT

An image forming apparatus includes an irradiation unit for irradiating an image carrier having a detection image with light; a light-receiving unit for receiving reflected light of the light irradiated by the irradiation unit and outputting a detection signal corresponding to a light-receiving amount of the reflected light including a specular-reflected light component; and a detection unit for detecting one of position information and density information of the detection image based on a signal corresponding to a difference between a value of the detection signal corresponding to the light-receiving amount of the reflected light from a first position where the detection image is formed and a value of the detection signal corresponding to the light-receiving amount
(Continued)

of the reflected light from a second position different from the first position.

18 Claims, 18 Drawing Sheets

(52) U.S. Cl.
CPC ............... *G03G 2215/0161* (2013.01); *G03G 2215/0164* (2013.01); *G06K 15/1878* (2013.01)

(56) References Cited

U.S. PATENT DOCUMENTS

| | | | |
|---|---|---|---|
| 9,049,313 | B2 | 6/2015 | Mukaibara et al. |
| 2009/0074476 | A1* | 3/2009 | Miyadera ............ G03G 15/0194 399/301 |
| 2010/0266302 | A1 | 10/2010 | Suzuki et al. |
| 2014/0226997 | A1 | 8/2014 | Koyama et al. |
| 2014/0308049 | A1 | 10/2014 | Yamaguchi et al. |

FOREIGN PATENT DOCUMENTS

| | | |
|---|---|---|
| JP | 2002-108030 A | 4/2002 |
| JP | 2003-076129 A | 3/2003 |
| JP | 2003-215883 A | 7/2003 |
| JP | 2004-212577 A | 7/2004 |
| JP | 2004-213032 A | 7/2004 |
| JP | 2004-361871 A | 12/2004 |
| JP | 2005-084206 A | 3/2005 |
| JP | 2005-241933 A | 9/2005 |
| JP | 2005-300918 A | 10/2005 |
| JP | 2006-350383 A | 12/2006 |
| JP | 2009-069767 A | 4/2009 |
| JP | 2009-258245 A | 11/2009 |
| JP | 2010-097209 A | 4/2010 |
| JP | 2010-180570 A | 8/2010 |
| JP | 2010-250049 A | 11/2010 |
| JP | 2011-175080 A | 9/2011 |
| JP | 2011-242441 A | 12/2011 |
| JP | 2012-103567 A | 5/2012 |
| JP | 2012-181379 A | 9/2012 |
| JP | 2012-181414 A | 9/2012 |

OTHER PUBLICATIONS

International Search Report and Written Opinion in PCT/JP2013/081575 dated Dec. 17, 2013.
Office Action dated Aug. 12, 2016 in Japanese Patent Application No. 2012-277443.

* cited by examiner

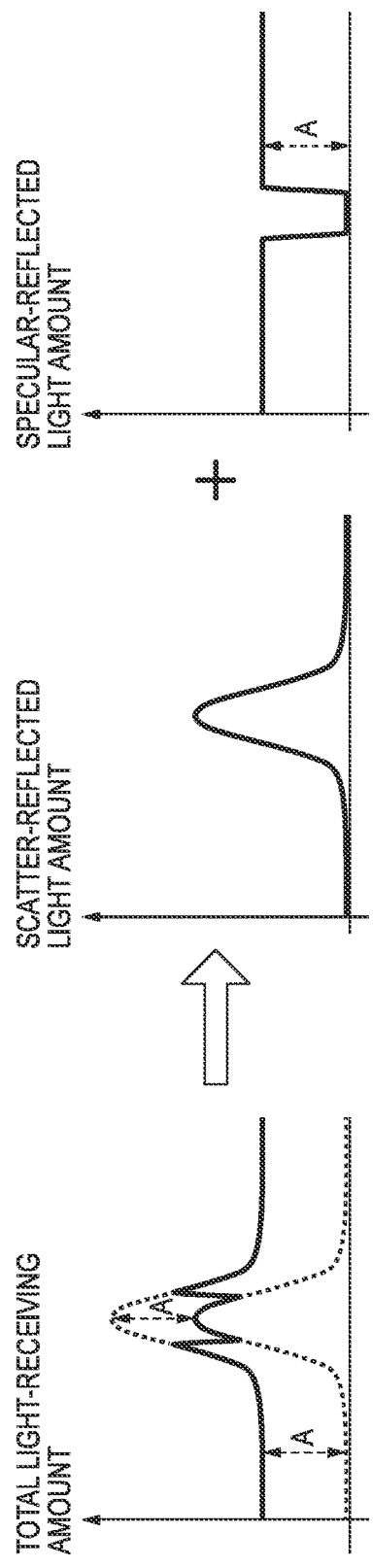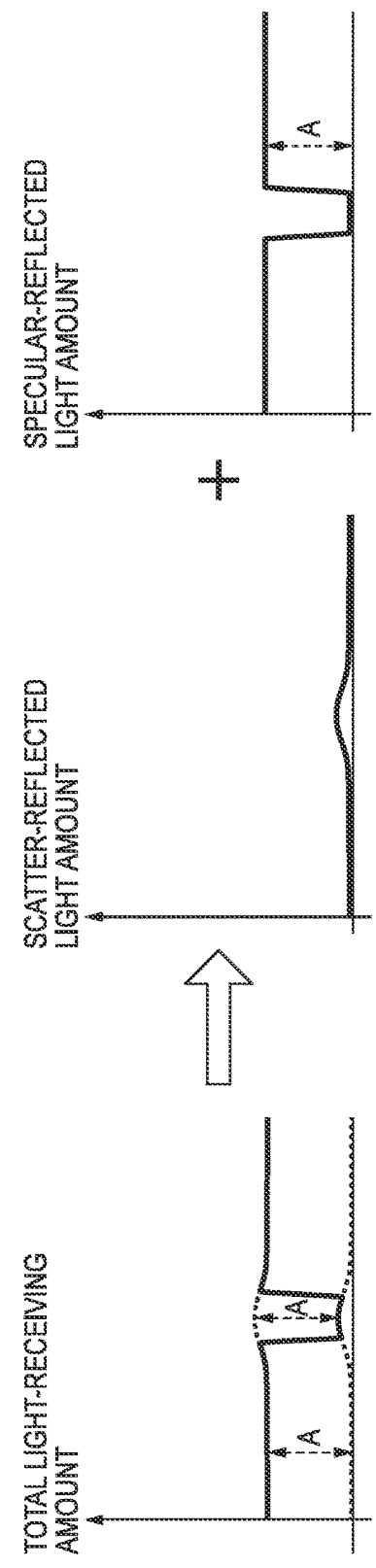

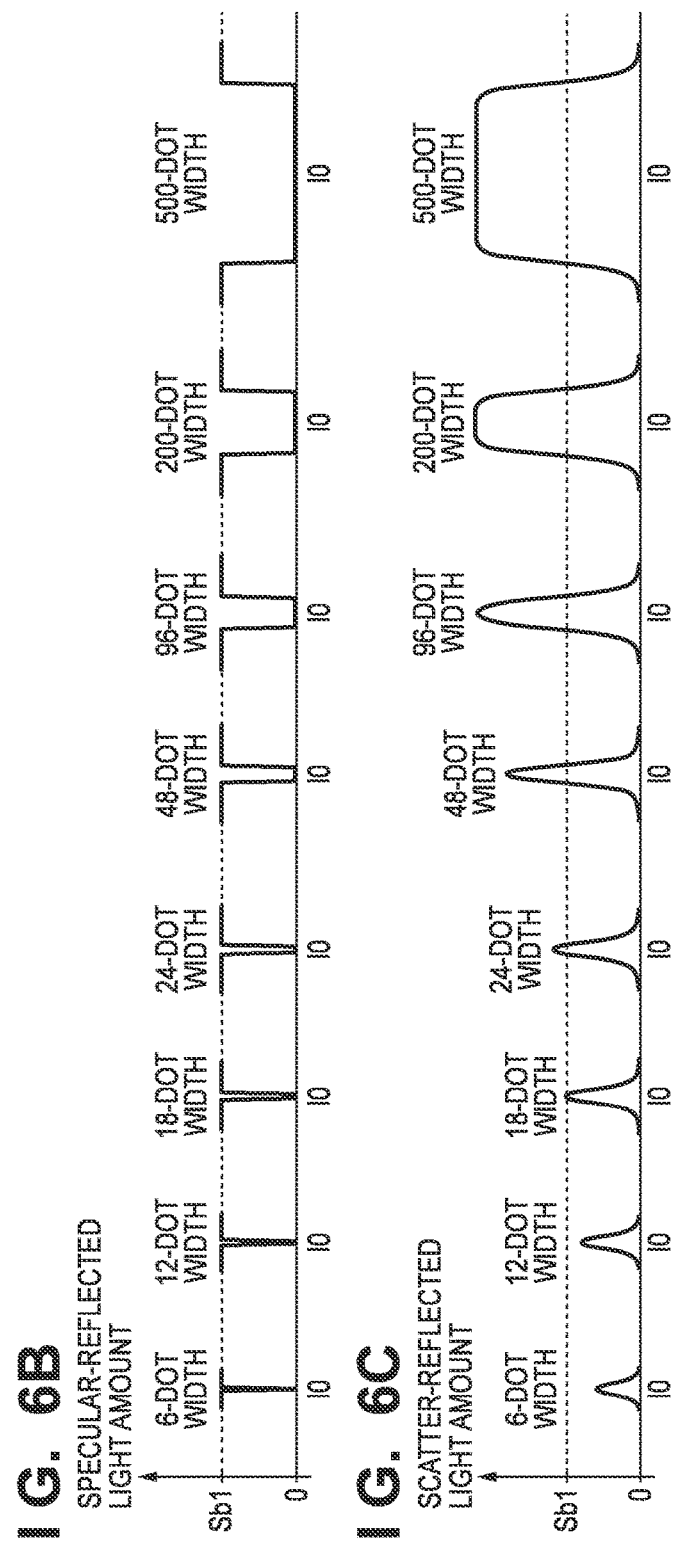
FIG. 6A TOTAL LIGHT-RECEIVING AMOUNT
FIG. 6B SPECULAR-REFLECTED LIGHT AMOUNT
FIG. 6C SCATTER-REFLECTED LIGHT AMOUNT

TOTAL LIGHT-RECEIVING AMOUNT

SPECULAR-REFLECTED LIGHT AMOUNT

SCATTER-REFLECTED LIGHT AMOUNT

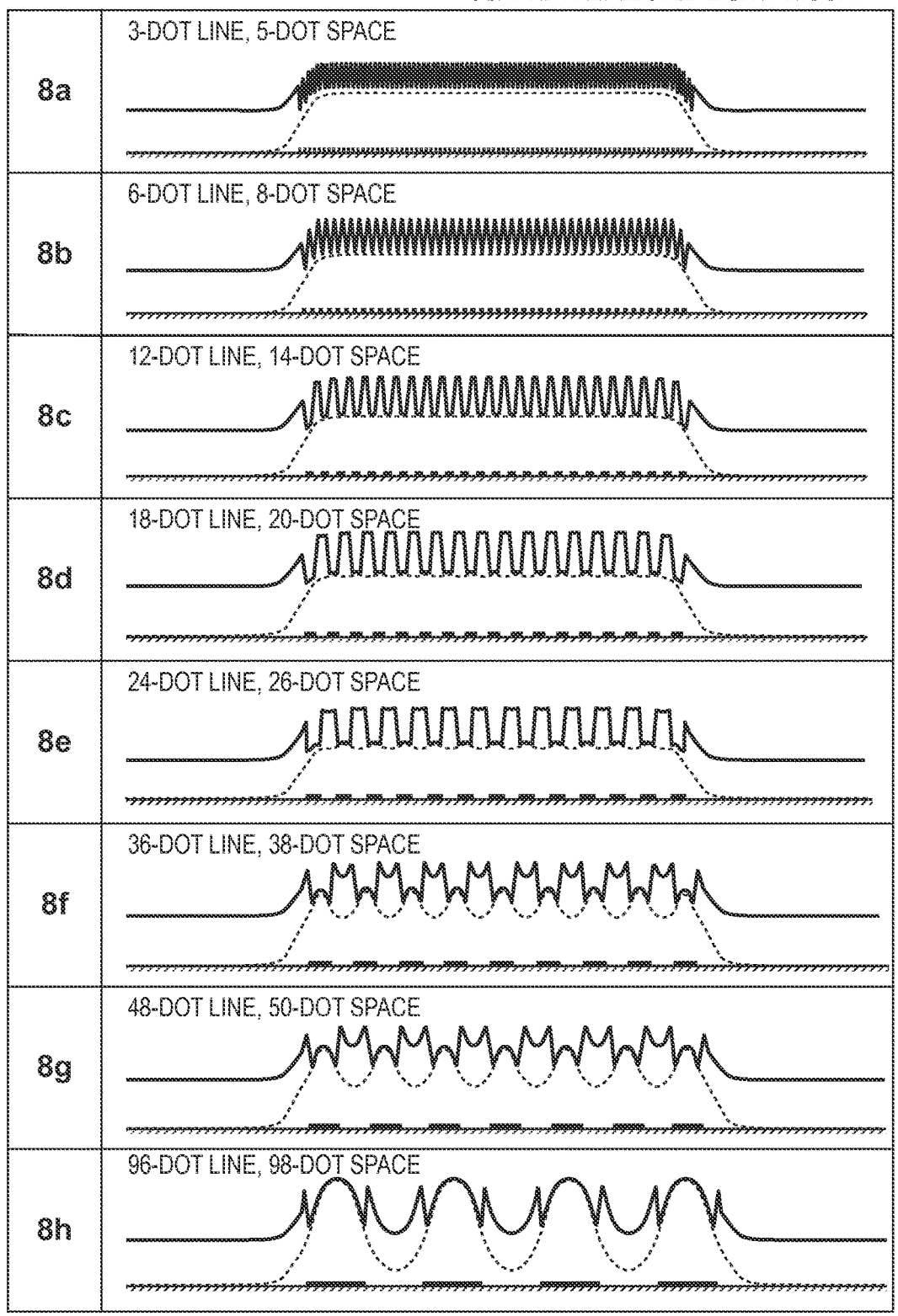

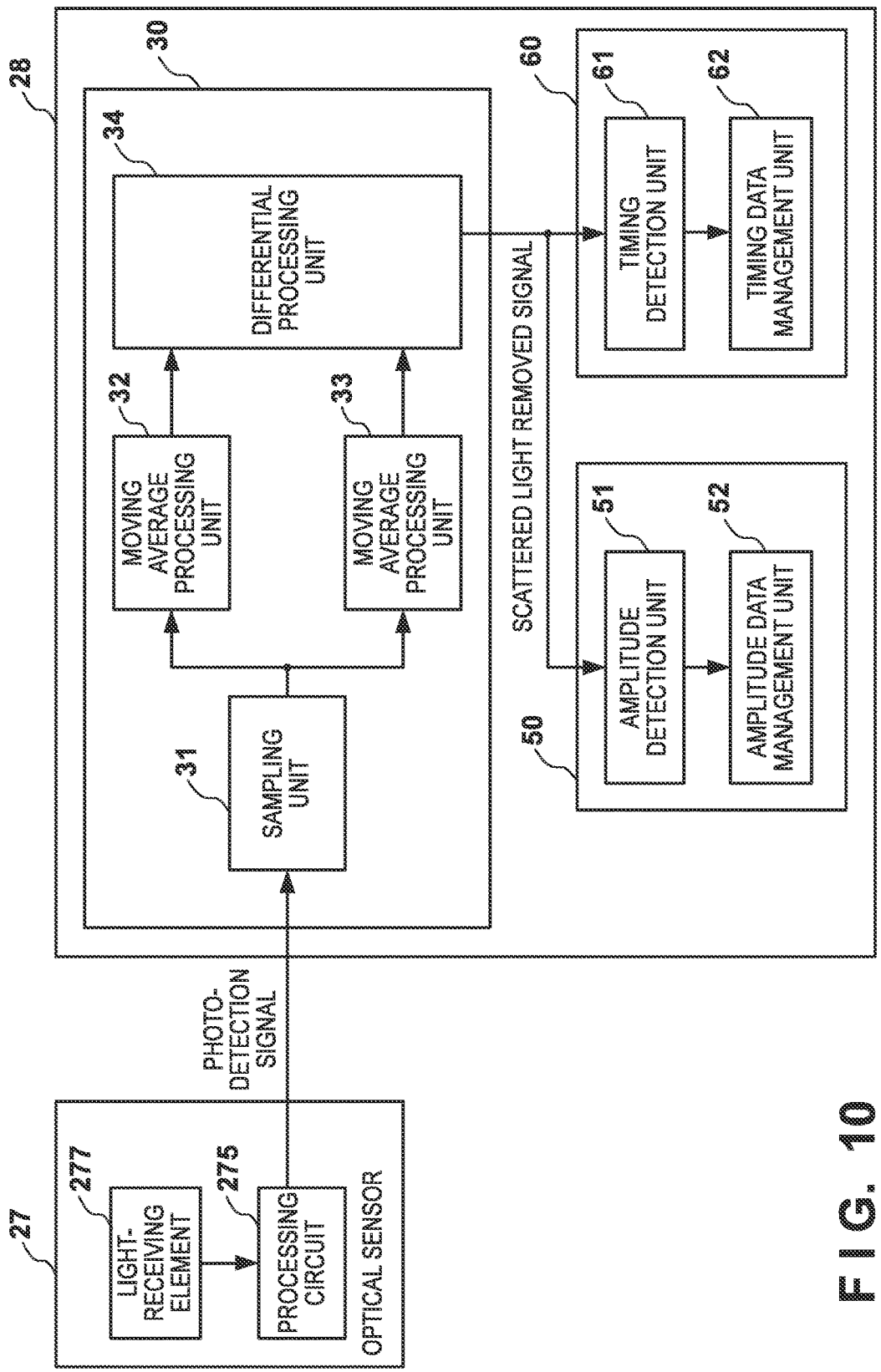
F I G. 10

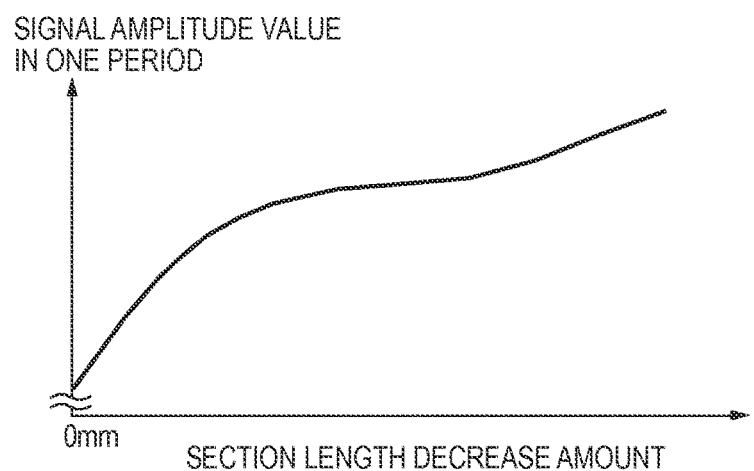
F I G. 17A
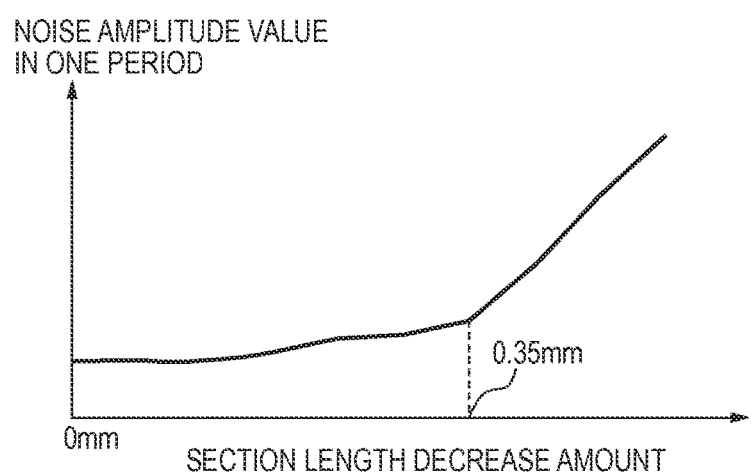
F I G. 17B
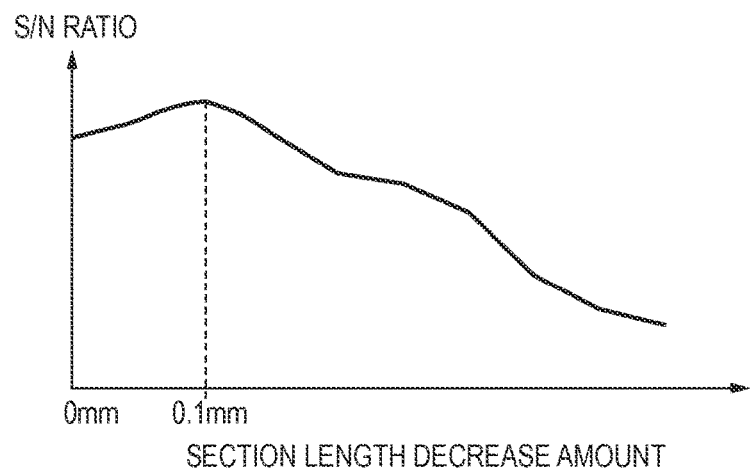
F I G. 17C

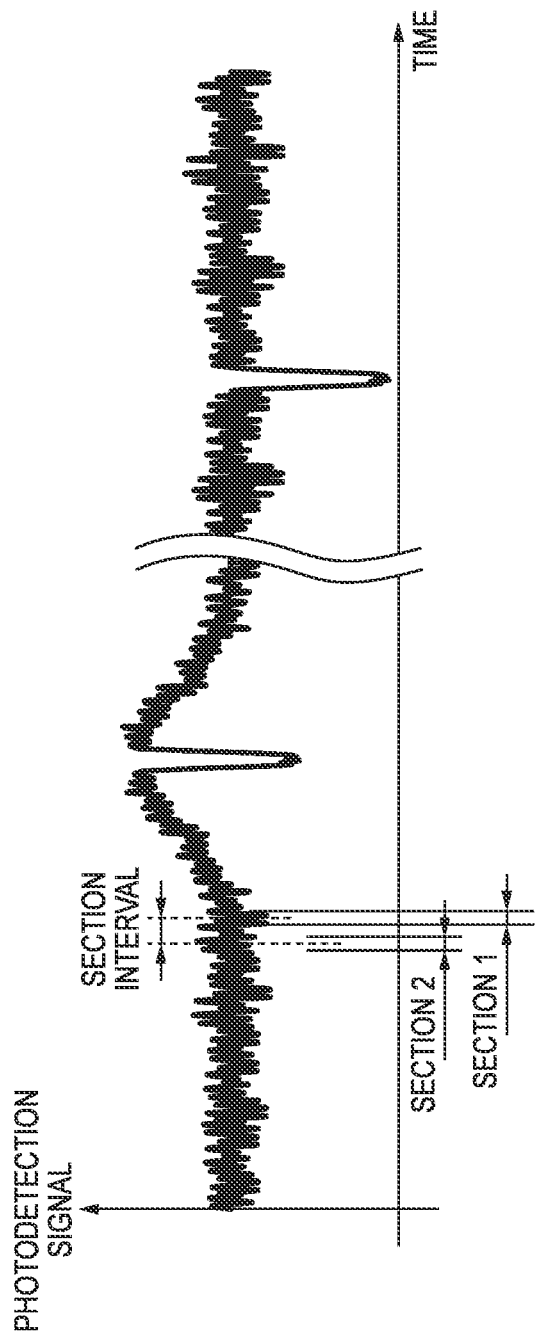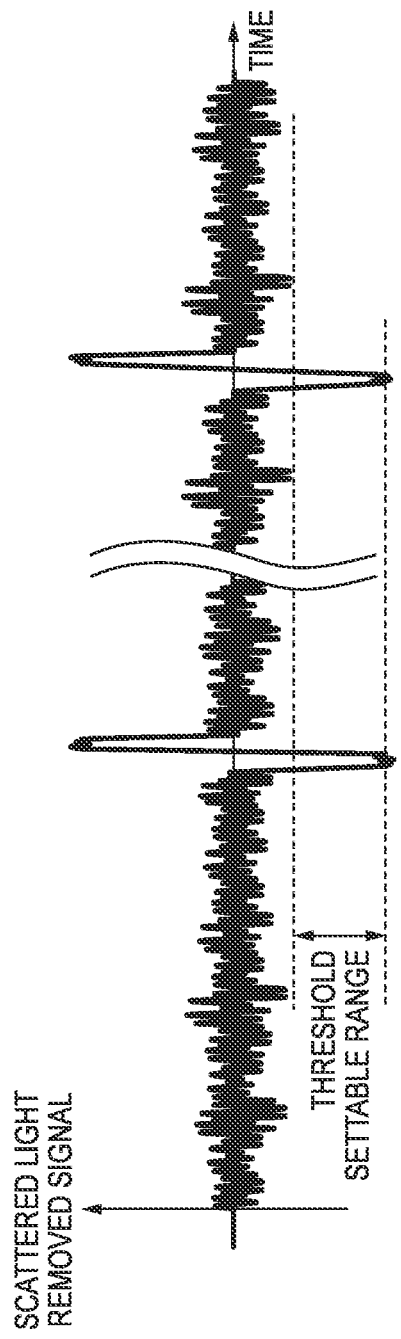

IMAGE FORMING APPARATUS AND DETECTION APPARATUS FOR DETECTING POSITION OR DENSITY INFORMATION OF DETECTION IMAGE

TECHNICAL FIELD

The present disclosure relates to a color misalignment and density detection technique in an image forming apparatus such as a color laser printer, a color copying machine, and a color facsimile apparatus mainly using an electrophotographic process.

BACKGROUND ART

The mainstream of recent electrophotographic image forming apparatuses is a tandem type that provides a photosensitive member for each color to speed up printing. In the tandem-type image forming apparatus, for example, a detection image that is a developing material image used to detect a color misalignment or density is formed on an intermediate transfer belt. The color misalignment or density is corrected by detecting reflected light from the detection image using an optical sensor.

Japanese Patent. Laid-Open No. 03-209281 discloses providing two sensors that respectively detect specular-reflected light (to also be referred to as mirror-reflected light) and scatter-reflected light from a toner image and controlling the image density in accordance with the output difference between the two sensors. Japanese Patent Laid-Open No. 2003-76129 discloses an optical sensor that detects both specular-reflected light and scatter-reflected light using a prism. In these methods, one light-receiving element detects only the scatter-reflected light components, and correction is performed by, for example, subtracting the scatter-reflected light from the sum of the scatter-reflected light and specular-reflected light detected by the other light-receiving element, thereby extracting only the specular-reflected light components. In a method of detecting the density from the extracted specular-reflected light components, not the scatter-reflected light from the toner but the specular-reflected light from the background is mainly detected. Hence, the density can be detected independently of the color of the developing material that generates a difference in the scatter-reflected light amount. It is also supposedly possible to attain a high detection capability for a highlight region that is sensitive to the human visual characteristic. In the method of Japanese Patent Laid-Open No. 03-209281, however, the error in correction processing of extracting only the specular-reflected light components becomes large. Japanese Patent Laid-Open No. 2005-300918 discloses reducing the effective spot diameter of specular-reflected light to lower the ratio of scatter-reflected light and thus improving the accuracy.

Consumption of the developing material by the detection image for color misalignment or density detection is required to be as low as possible. That is, the detection image is preferably made as small as possible. Even for a small detection image, a sensor having a high spatial resolution is necessary to accurately detect the density. Japanese Patent Laid-Open No. 2005-241933 discloses a sensor having a smaller irradiation area on the light emission side.

When the spot diameter of specular-reflected light is reduced in the conventional optical sensor, a variation of the light-emitting element position in the optical sensor or a mechanical variation of the converging mechanism greatly affects the yield in the manufacture or the detection accuracy. For example, the higher the spatial resolution of the optical sensor is, the smaller the converging mechanism needs to be. According to Japanese Patent Laid-Open No. 2005-241933, the spot diameter of the specular-reflected light is limited to about 1 mm when the variation in the manufacture and the like are taken into consideration.

SUMMARY OF INVENTION

According to an aspect of the present invention, an image forming apparatus includes: an image carrier; forming means for forming a detection image made of a developing material on the image carrier; irradiation means for irradiating the image carrier having the formed detection image with light; light-receiving means for receiving reflected light of the light irradiated by the irradiation means and outputting a detection signal corresponding to a light-receiving amount of the reflected light including a specular-reflected light component; and detection means for detecting one of position information and density information of the detection image based on a signal corresponding to a difference between a value of the detection signal corresponding to the light-receiving amount of the reflected light from a first position where the detection image is formed and a value of the detection signal corresponding to the light-receiving amount of the reflected light from a second position different from the first position during a time when the detection image formed on the image carrier passes through an irradiation region of the irradiation means.

Further features of the present invention will become apparent from the following description of exemplary embodiments with reference to the attached drawings.

BRIEF DESCRIPTION OF DRAWINGS

FIGS. 5A and 5B are explanatory views of the difference in reflected light caused by the difference between the colors of developing materials;

FIGS. 6A to 6C are views showing the relationship between the reflected light and the line width of a detection image when the gap distance is 1 mm;

FIG. 8 is a view showing the relationship between the reflected light and the line and space widths of the detection image when the gap distance is 1 mm;

FIG. 10 is a block diagram showing the exemplary arrangement of a detection system according to an embodiment;

FIGS. 17A to 17C are explanatory views of the relationship between the section length decrease amount and the S/N ratio; and FIGS. 18A and 18B are explanatory views of the relationship between noise and the threshold settable range.

DESCRIPTION OF EMBODIMENTS

Figure 1A:
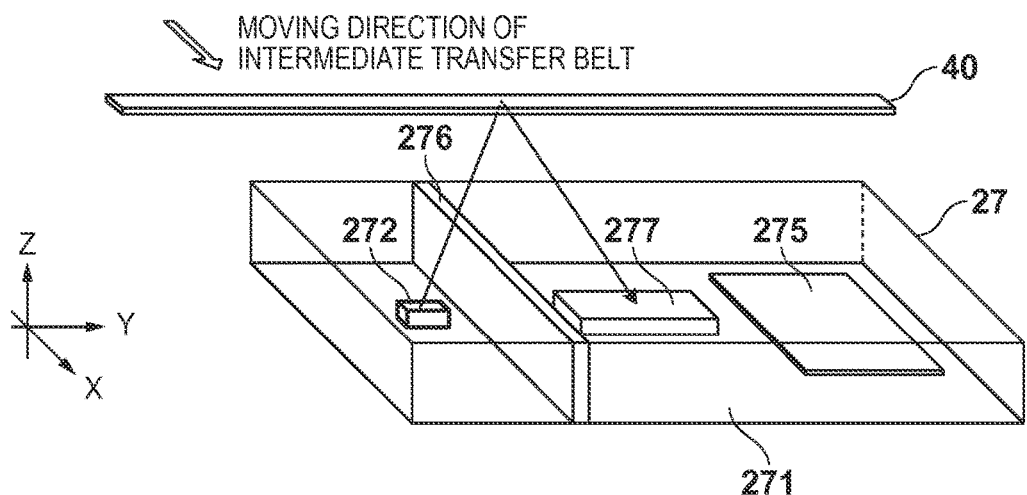
FIGS. 1A to 1C are views showing the reflected state of light emitted by an optical sensor according to an embodiment.

Exemplary embodiments of the present invention will now be described with reference to the accompanying drawings. Note that the constituent elements unnecessary for the description of the embodiments are not illustrated in the following drawings. The same reference numerals denote the similar constituent elements throughout the drawings.

First Embodiment

Figure 15:
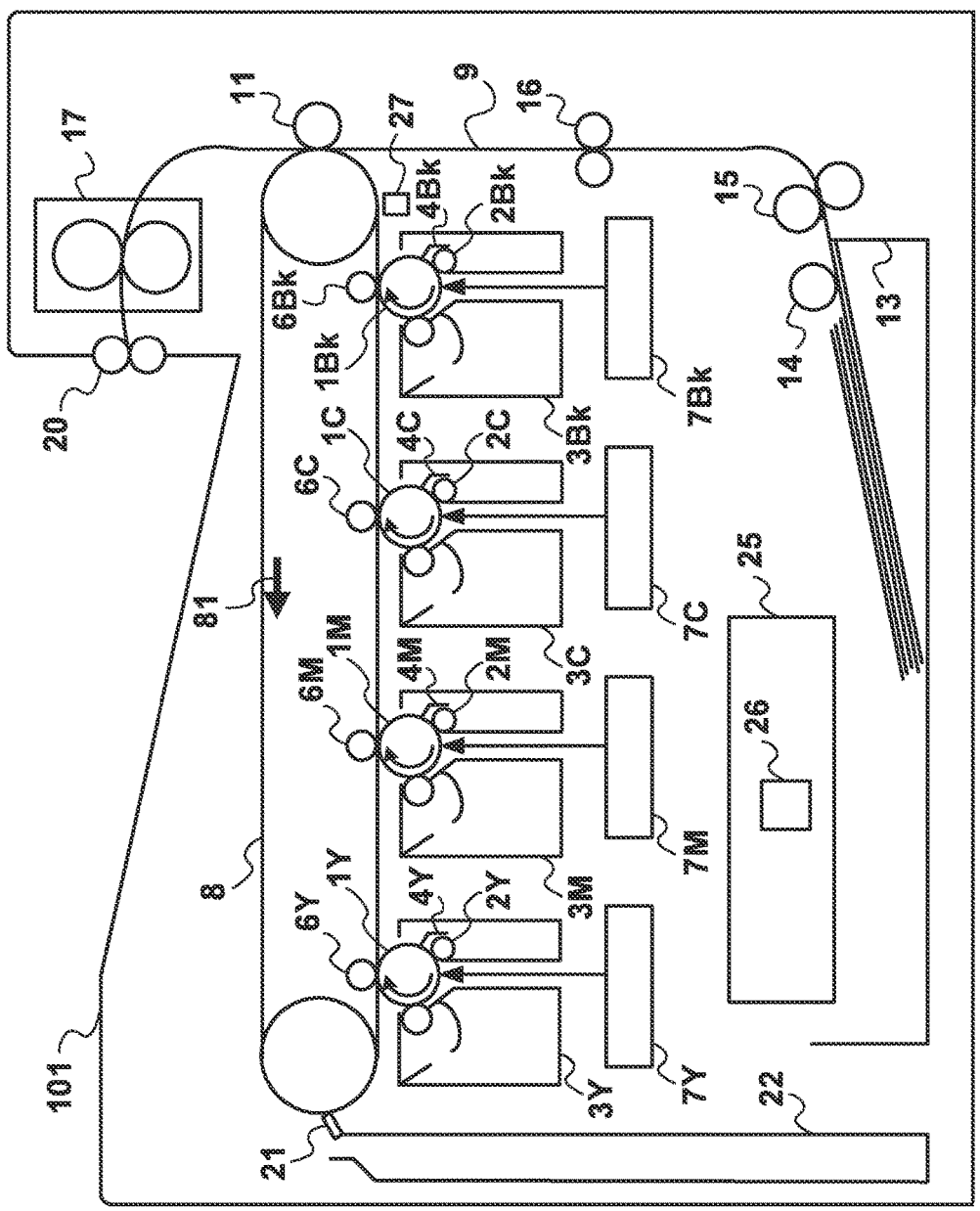
FIG. 15 is a sectional view showing the schematic arrangement of an image forming apparatus according to an embodiment.

An image forming apparatus 101 according to this embodiment will be described first with reference to FIG. 15. Note that the suffixes Y, M, C, and Bk of the reference numerals in FIG. 15 indicate that toners serving as developing materials for the corresponding members are yellow, magenta, cyan, and black, respectively. Note that reference numerals without the suffixes Y, M, C, and Bk are used when the colors need not be distinguished in the following description. A charging unit 2 uniformly charges a photosensitive member 1 serving as an image carrier rotated in the direction of an arrow in FIG. 15. An exposure unit 7 irradiates the photosensitive member 1 with a laser beam to form an electrostatic latent image on it. A developing unit 3 supplies a developing material to the electrostatic latent image by applying a developing bias and changes the electrostatic latent image to a toner image (developing material image) that is a visible image. A primary transfer roller 6 transfers the toner image on the photosensitive member 1 to an intermediate transfer belt 8 by a primary transfer bias. Note that the intermediate transfer belt 8 is rotated in the direction of an arrow 81. The photosensitive members 1 transfer the toner images to the intermediate transfer belt 8 in a superimposed manner, thereby forming a color image. A cleaning blade 4 removes the toner remaining on the photosensitive member 1 without being transferred to the intermediate transfer belt 8.

Conveyance rollers 14, 15, and 16 convey a printing medium in a cassette 13 to a secondary transfer roller 11 along a conveyance path 9. The secondary transfer roller 11 transfers the toner image on the intermediate transfer belt 8 to the printing medium by a secondary transfer bias. Note that the toner remaining on the intermediate transfer belt 8 without being transferred to the printing medium is removed by a cleaning blade 21 and collected by a waste toner collection container 22. A fixing unit 17 heats and pressurizes the printing medium with the transferred toner image to fix the toner image. The printing medium is then discharged by conveyance rollers 20 out of the apparatus. Note that an engine control unit 25 includes a microcontroller 26 and performs sequence control of various kinds of driving sources (not shown) of the image forming apparatus or various kinds of control using sensors. An optical sensor 27 is provided at a position facing the intermediate transfer belt 8.

For example, in a tandem-type image forming apparatus, the mechanical dimensions deviate from the design values due to assembly errors, part tolerance, thermal expansion of parts, and the like upon manufacturing the apparatus, resulting in displacement for each color. Hence, a detection image used to detect the color misalignment of each color is formed on the intermediate transfer belt 8 or the like, and reflected light from the formed detection image is detected by the optical sensor 27. The print start positions in the main scanning direction and sub-scanning direction and the image clock are adjusted for each color based on the detection result, thereby correcting the color misalignment. Additionally, in the image forming apparatus, the tint, density, and the like of the output image may change due to temporal changes or continuous printing. To correct this variation, density control is performed. In the density control, the detection image used to detect the density of each color is formed on the intermediate transfer belt 8 or the like, and reflected light from the formed detection image is detected by the optical sensor 27. The detection result is fed back to each voltage condition or a process formation condition such as laser power, thereby correcting the maximum density or halftone characteristic of each color. Density detection by the optical sensor 27 is generally done using a method of irradiating the detection image with a light source and detecting the intensity of reflected light by a light-receiving element. A signal corresponding to the intensity of the reflected light is processed by the microcontroller 26 and fed back to the process formation conditions. Maximum density control aims at maintaining predetermined color balance between colors and preventing spattering or a fixing failure of a color-overlaid image caused by excessive toner application. On the other hand, halftone control aims at preventing natural image formation from failing due to the shift of the output density with respect to the input image signal caused by a nonlinear input/output characteristic.

Details of the optical sensor 27 according to this embodiment will be described below with reference to FIG. 1A. FIG. 1A is a perspective view showing the relationship between the optical sensor 27 and a detection image 40. Note that the detection image 40 shown in FIG. 1A is a toner image made of a toner and including one line in a direction perpendicular to the moving direction of the intermediate transfer belt 8. Note that although the one line will be explained as a solid line in the following embodiment, it may be a discontinuous line such as a dotted line or a broken line. The optical sensor 27 according to this embodiment includes a light-emitting element 272, a light-receiving element 277, a processing circuit 275, and a light blocking wall 276 arranged on a package board 271. A normal light-emitting element used to detect color misalignment and density incorporates a reflecting plate to collect light diffused like a flare from the light-emitting element. A shell-shaped light-emitting element includes a condenser lens as well. On the other hand, the optical sensor 27 according to this embodiment includes neither a reflecting plate nor a condenser lens but only an LED chip, thereby irradiating the intermediate transfer belt with divergent beams of a point source. The element on the light-receiving side similarly uses no condenser lens but, for example, a photodiode that outputs a current corresponding to a light-receiving amount. That is, reflected light from the intermediate transfer belt 8 enters the light-receiving element 277 without passing through an optical member configured to converge or condense the light. The processing circuit 275 performs control of the light-emitting element 272 that performs light irradiation and processing of the signal detected by the light-receiving element 277, and outputs the processed signal to the microcontroller 26. Note that the optical sensor 27 is packaged by a resin and glass. The light blocking wall 276 is provided to prevent the irradiation light from the light-emitting element 272 from entering the light-receiving element 277 directly as stray light or after being reflected by the interface of the package.

The image forming apparatus causes the light-emitting element 272 to irradiate the intermediate transfer belt 8 and the detection image 40 formed on the intermediate transfer belt with light and the light-receiving element 277 to receive reflected light from them, thereby detecting color misalignment and density. Basically, the color misalignment amount is detected by detecting the relative pass timing of the detection image 40 of each color. The toner density is determined by detecting the average light amount from the detection image 40 formed in halftone. The color misalignment and density are detected by monitoring the specular-reflected light components from the intermediate transfer belt 8. The image forming apparatus according to this embodiment uses four color toners. The light absorption/reflection characteristic changes depending on the toner color. For example, infrared light is mostly absorbed by the black toner and scatter-reflected by the toners of the remaining colors. Red light is mostly absorbed by the black and cyan toners and scatter-reflected by the toners of the remaining colors.

That is, it is necessary to perform processing of removing the scattered light components by the detection image 40 in a state in which the toners that generate a large amount of scatter-reflected light and the toners that less or hardly generate scatter-reflected light. To do this, in conventional color misalignment or density control, the optical sensor includes a converging mechanism, and a light-receiving element configured to detect only the scatter-reflected light components is separately provided. However, the optical sensor 27 of this embodiment includes no converging mechanism, and removes the scatter-reflected light components by the detection image 40. The optical sensor 27 of this embodiment includes no converging mechanism and can therefore be downsized to a fraction of the conventional size.

Figure 1B:
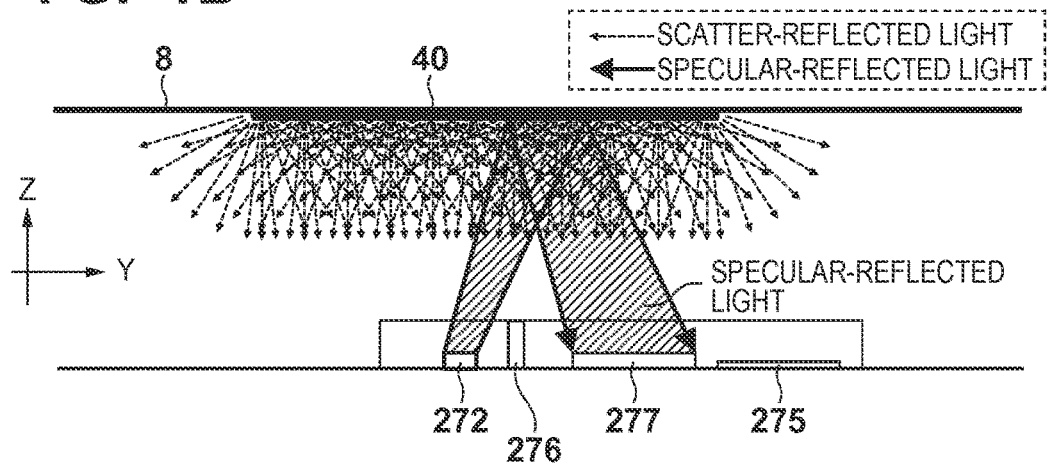
Figure 1C:
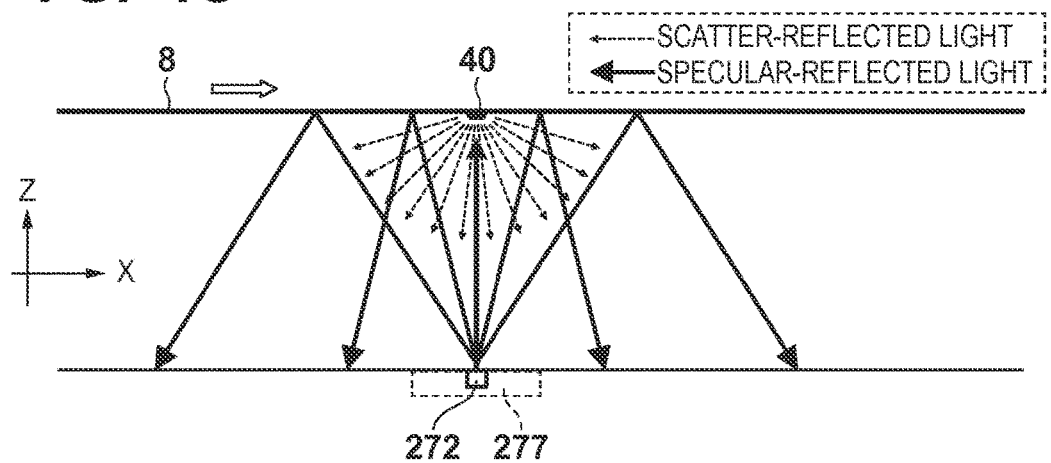

The state of reflected light from the intermediate transfer belt 8 and the detection image 40 on the intermediate transfer belt will be described below in detail with reference to FIGS. 1B and 10. FIG. 1B is a view from the X-axis direction of FIG. 1A. The intermediate transfer belt 8 travels from the far side to the near side in the drawing. FIG. 1C is a view from the Y-axis direction of FIG. 1A. The intermediate transfer belt 8 travels in the direction of a hollow arrow in the drawing. Light emitted by the light-emitting element 272 is mainly specular-reflected by the surface of the intermediate transfer belt 8 and detected by the light-receiving element 277. This specular-reflected light is indicated by the solid arrows. Note that when the light-emitting element 272 is a point source, and the arrangement relationship makes the optical path length of the incident light to the intermediate transfer belt 8 and that of reflected light equal to each other, the width of the reflected light that enters the light-receiving element 277 is twice larger than the length on the intermediate transfer belt, as shown in FIG. 1B. On the other hand, the light emitted by the light-emitting element 272 is mainly scatter-reflected by the toner line of the detection image 40 formed on the intermediate transfer belt 8. This scatter-reflected light is indicated by the broken arrows. Note that as for the scatter reflection, the irradiation light from the light-emitting element 272 to the detection image 40 is not illustrated to avoid cumbersomeness, and the scatter-reflected light components detected by the light-receiving element 277 are indicated by short broken arrows to avoid cumbersomeness of the drawing.

For example, the arrangement distance between the light-emitting element 272 and the light-receiving element 277 can be set to about 1 to 2 mm, and the distance (to be referred to as a gap distance hereinafter) between the optical sensor 27 and the intermediate transfer belt 8 can be set to 1 to 5 mm. However, the present invention is not limited to these values, and other values are also usable.

Figure 3A:
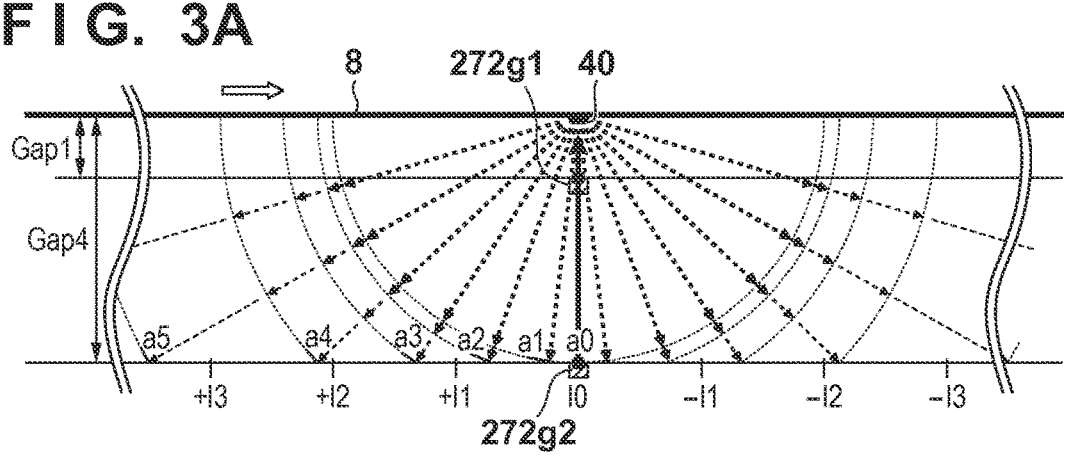
FIGS. 3A to 3D are explanatory views of scatter-reflected light detected by the optical sensor.
Figure 3B:
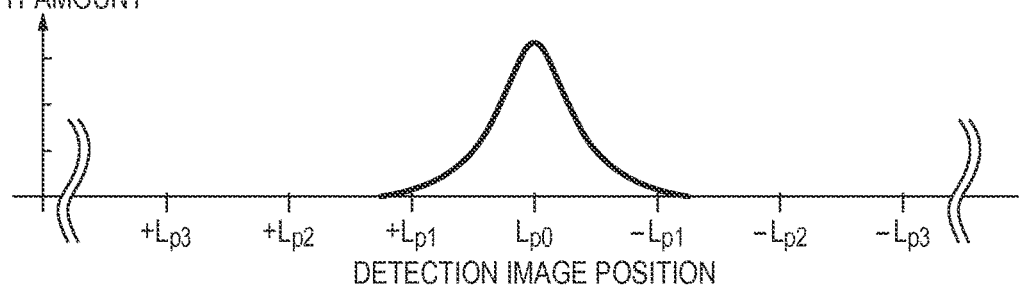
Figure 3C:
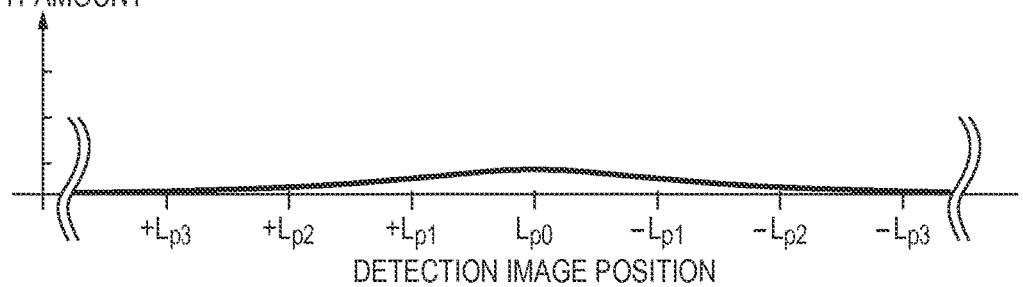
Figure 3D:
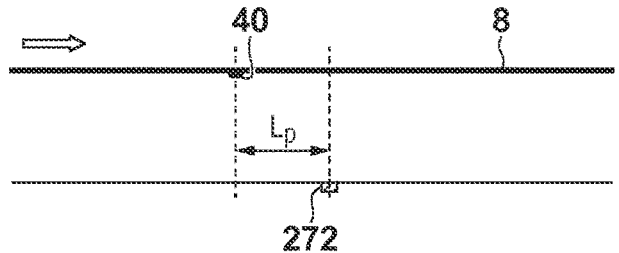

Detection of scatter-reflected light by toner will be described next in detail. FIG. 3A shows scatter-reflected light from the detection image 40 on the intermediate transfer belt 8 shown in FIG. 1C in more detail. The line of the detection image 40 reflects the irradiation light in various directions. The detection characteristic changes depending on the distance between the optical sensor 27 and the intermediate transfer belt 8. FIG. 3A shows two gap distances Gap1 and Gap4. Note that the gap distance Gap1 is 1 mm, and the gap distance Gap4 is 4 mm. Reference numeral 272g1 represents a light-emitting element for the gap distance Gap1; and 272g2, a light-emitting element for the gap distance Gap4. FIGS. 3B and 3C show the scatter-reflected light amount received by the light-receiving element 277 when the detection image 40 is caused to pass through the irradiation region of the light-emitting element 272 by rotating the intermediate transfer belt 8. Note that +Lp3 to −Lp3 in FIGS. 3B and 3C indicate the arrangement distances between the light-emitting element 272 and the detection image 40 shown in FIG. 3D. As shown in FIG. 3B, at the gap distance Gap1, scatter-reflected light was detected when the arrangement distance approximately ranged from +Lp1 to −Lp1. On the other hand, as shown in FIG. 3C, at the gap distance Gap4, scatter-reflected light was detected when the arrangement distance approximately ranged from +Lp3 to −Lp3. At Lp0 corresponding to an arrangement distance of 0, the scatter-reflected light amount at Gap4 was much smaller than at Gap1. That is, as the gap distance between the optical sensor 27 and the intermediate transfer belt 8 becomes long, the scatter-reflected light amount by the detection image 40 decreases, but scatter-reflected light from the detection image 40 farther apart is detected, as can be seen.

Figure 4A:
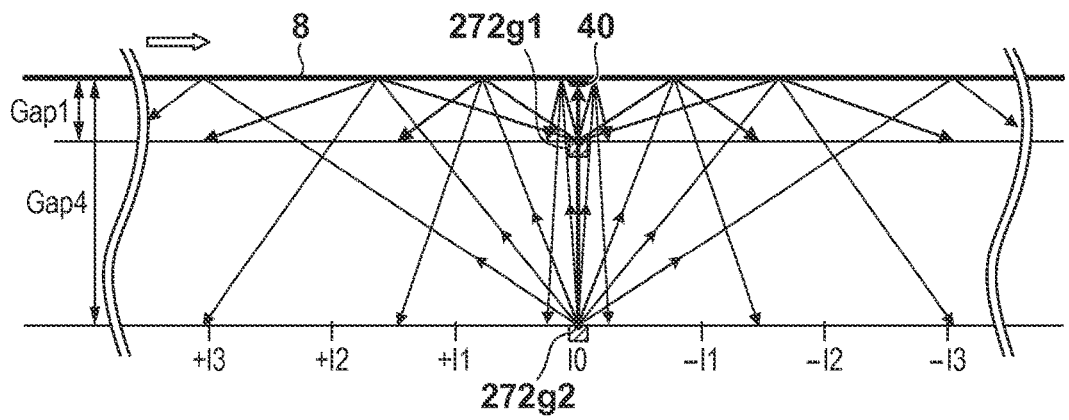
FIGS. 4A to 4C are explanatory views of specular-reflected light detected by the optical sensor.
Figure 4B:
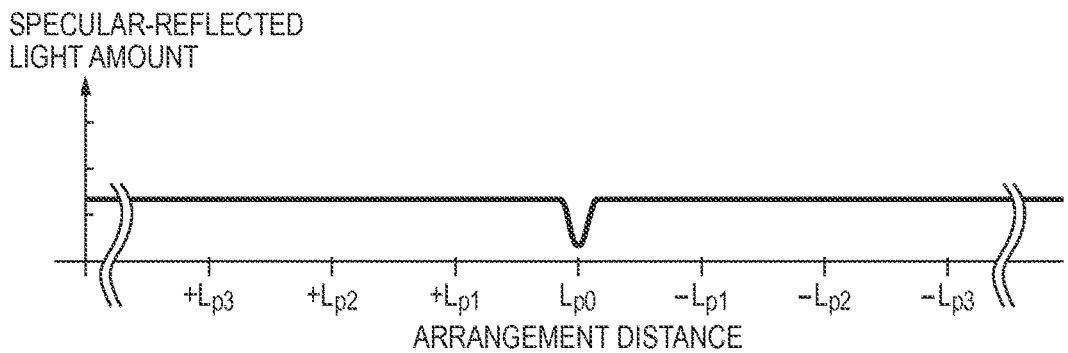
Figure 4C:
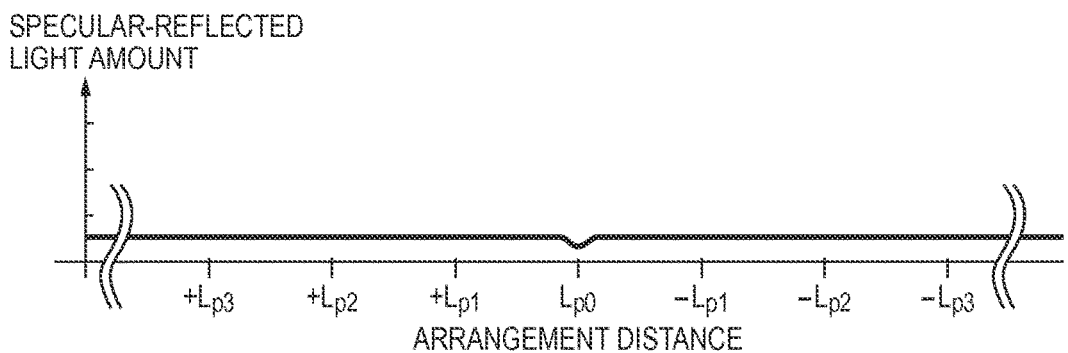

Detection of specular-reflected light will be described next in detail. FIG. 4A shows specular-reflected light from the intermediate transfer belt 8 shown in FIG. 1C in more detail. Note that the two gap distances shown in FIG. 4A are the same as those for the scatter-reflected light shown in FIG. 3A. FIGS. 4B and 4C show the specular-reflected light amount received by the light-receiving element 277 when the detection image 40 is caused to pass through the irradiation region of the light-emitting element 272 by rotating the intermediate transfer belt 8. Note that +Lp3 to −Lp3 in FIGS. 4B and 4C indicate the arrangement distances shown in FIG. 3D. As shown in FIGS. 4B and 4C, at both the gap distances Gap1 and Gap4, a decrease in the specular-reflected light was detected near the arrangement distance Lp0. However, widening of the detectable range depending on the gap distance did not occur, unlike the scatter-reflected light. Note that the decrease in the specular-reflected light at the arrangement distance Lp0 occurs because the irradiation light is absorbed or scatter-reflected when the detection image 40 passes through.

As described above, the scatter-reflected light and specular-reflected light from the intermediate transfer belt 8 and the detection image 40 formed on it change depending on the arrangement distance between the optical sensor 27 and the detection image 40. In addition, the scatter-reflected light is affected by the gap distance, whereas the specular-reflected light is rarely affected by the gap distance.

A waveform (combined waveform of scatter-reflected light and specular-reflected light) obtained when the optical sensor 27 detects the detection image 40 including one line will be described with reference to FIGS. 5A and 5B. FIG. 5A shows the relationship between the arrangement distance and the light-receiving amount of the light-receiving element 277 when the detection image 40 is formed by toner that generates a large amount of scatter-reflected light. Note that the arrangement distance indicates the distance Lp shown in FIG. 3D. Note that the length of the line in the sub-scanning direction, that is, in the moving direction of the surface of the intermediate transfer belt 8 is set to 48 dots at 600 dpi. FIG. 5B shows the relationship between the arrangement distance and the total light-receiving amount of the light-receiving element 277 when the detection image 40 is formed by, for example, black toner that generates a very small amount of scatter reflection. FIGS. 5A and 5B also show the light-receiving amounts of scatter-reflected light and specular-reflected light in the respective cases. The detection image 40 shown in FIG. 5A generates a larger amount of scatter reflection than the detection image 40 shown in FIG. 5B. For this reason, the total light-receiving amount of the light-receiving element 277 is largely affected by the scatter-reflected light as compared to FIG. 5B. Note that the waveforms shown in FIGS. 5A and 5B change depending on the width of the line of the detection image 40.

Figure 7A:
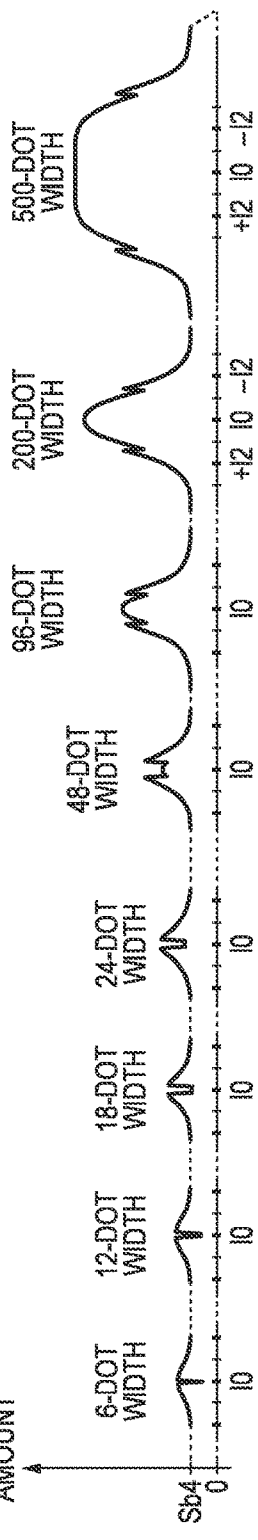
FIGS. 7A to 7C are views showing the relationship between the reflected light and the line width of the detection image when the gap distance is 4 mm.
Figure 7B:
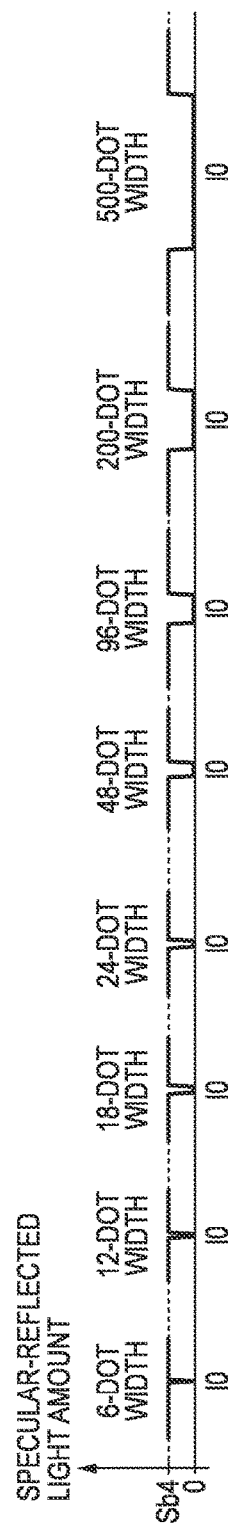
Figure 7C:
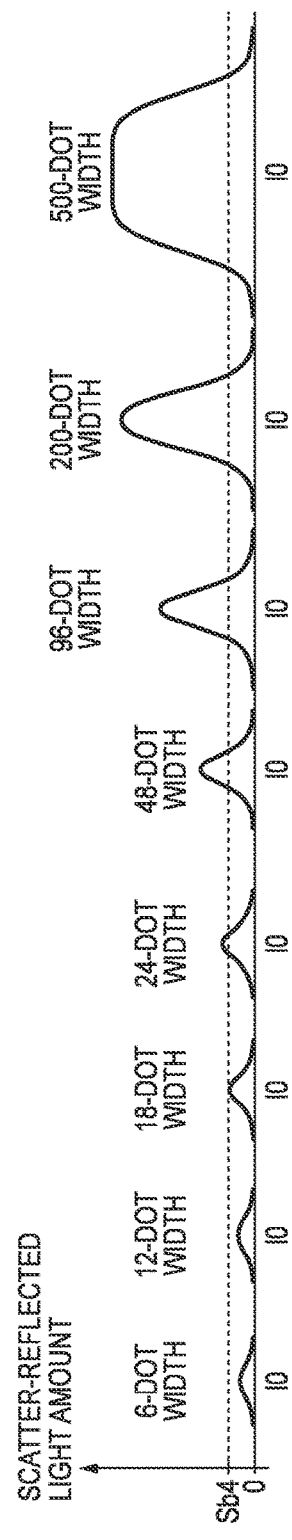

FIG. 6A shows a waveform representing the total light-receiving amount of the optical sensor 27 when the gap distance is set to 1 mm, and the detection image 40 is moved in the detection region of the optical sensor 27. Note that the detection image 40 is formed using toner of a color that generates a large amount of scatter-reflected light, and the sub-scanning direction width is changed from 6 dots to 500 dots. FIG. 6B shows the specular-reflected light component in FIG. 6A, and FIG. 6C shows the scatter-reflected light component in FIG. 6A. Note that a position 10 under each waveform corresponds to an arrangement distance of 0. As is apparent from FIG. 6B, in specular-reflected light, as the line width of the detection image 40 increases, the range in which the received specular-reflected light amount decreases becomes wide. However, except that, the light-receiving amount does not change so largely. Note that Sb1 in FIGS. 6A to 6C is the same or almost the same as the reflected light amount from the surface of the intermediate transfer belt 8 itself. On the other hand, in scatter-reflected light, as the line width of the detection image 40 increases, the light-receiving amount also increases. When the line width of the detection image 40 is about 200 dots, the amplitude is saturated. After that, even when the line width of the detection image 40 increases, the maximum value of the light-receiving amount does not change, and the duration of the maximum value becomes long. Note that the increase in the duration of the maximum value corresponds to an increase in the detection time at the maximum value in the light-receiving element 277. Hence, as for the scatter-reflected light, the maximum value changes up to a predetermined line width. However, when the line width exceeds a predetermined value, the maximum value of the light-receiving amount does not change anymore. FIGS. 7A to 7C show waveforms when, out of the conditions under which the waveforms shown in FIGS. 6A to 6C are acquired, only the gap distance is changed from 1 mm to 4 mm. Sb4 in FIGS. 7A to 7C corresponds to the specular-reflected light amount from the surface of the intermediate transfer belt 8. As is apparent from FIG. 7C, when the gap distance increases, scatter-reflected light from the detection image 40 farther apart can be detected. In addition, when the line width of the detection image 40 is small, the maximum value of the scatter-reflected light amount is also smaller than that for a shorter gap distance. However, when the line width reaches the value at which the scatter-reflected light amount is saturated, the difference in the scatter-reflected light amount depending on the gap distance becomes considerably small, as can be seen. On the other hand, as for specular-reflected light, when the gap distance increases, the light-receiving amount simply decreases. Hence, when the gap distance is increased, and the line width of the detection image 40 is decreased, the ratio of the scatter-reflected light components in the total light-receiving amount rises.

Figure 2:
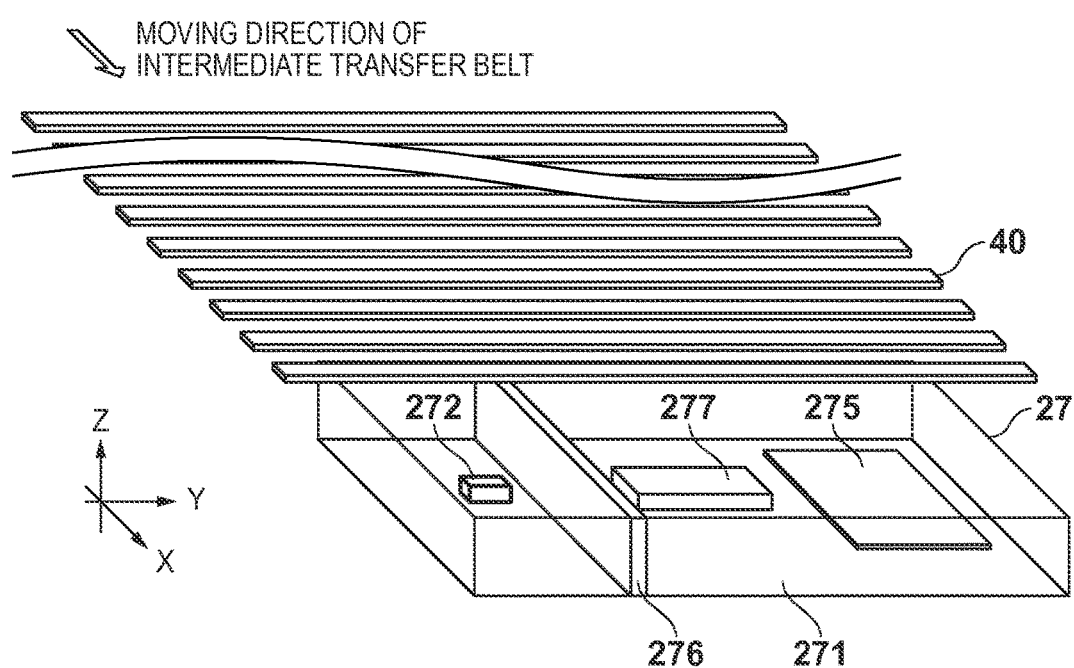
FIG. 2 is a perspective view showing the optical sensor and a detection image including a plurality of lines according to an embodiment.

A waveform detected by the optical sensor 27 when the striped detection image 40 including a plurality of lines shown in FIG. 2 is formed will be described next. Note that although the lines will be explained as solid lines in the following embodiment, they may be discontinuous lines such as broken lines or dotted lines. FIG. 8 shows a time-rate change in the total light-receiving amount of the light-receiving element 277 when the striped detection image 40 passes through the irradiation range of the light-emitting element 272. Note that FIG. 8 illustrates a total of eight waveforms obtained by setting the sub-scanning direction length of the detection image 40 to about 100 mm and changing the line width and the width of the region (to be referred to as a space hereinafter) between the lines. Note that in waveforms 8a to 8h, the space width is larger than the line width by two dots so as to make the line width and the space width of the actually formed detection image 40 almost equal. Note that for the waveforms 8a to 8h, signal waveforms and the lines of the detection image 40 for understanding of the relationship between the line width and the space width of the detection image 40 are illustrated under the signal waveforms.

In the detection image 40 including a plurality of lines, the scatter-reflected light components from the lines interfere with each other. When the line pitch is large, the scatter-reflected light components interfere but do not become even, and the light-receiving amount oscillates. For example, when the pitch is larger than the line pitch of the waveform 8f, the variation in the light-receiving amount of the scatter-reflected light is very large. Note that the line pitch is the distance between the centers of adjacent lines, which equals the sum of the line width and the space width. In the line pitch of the waveform h, the influence of scatter-reflected light from an adjacent line is very little. To the contrary, when the pitch is smaller than the line pitch of the waveform 8c, scatter-reflected light amount is almost even. Note that the variation in the received scatter-reflected light amount mainly depends on the space width. Even if the line width is 12 dots, the scatter-reflected light amount oscillates at the period of the line pitch when the space width is 30 dots. That is, when the gap distance is 1 mm, the variation in the scatter-reflected light can be suppressed by setting the space width to about 15 dots or less. For example, in this embodiment, the space width is set such that the variation in the scatter-reflected light from the detection image 40 falls within a predetermined amount. More specifically, the space width is set such that the difference between the maximum value and the minimum value where the scatter-reflected light in FIG. 8 oscillates falls within a predetermined amount. This makes the scatter-reflected light components in the total light-receiving amount almost constant, oscillation caused by attenuation of specular-reflected light components by the lines of the detection image 40 becomes dominant in the oscillation of the total light-receiving amount, and the scatter-reflected light components can easily be removed.

Note that the lines shown in FIG. 8 are formed at a density of almost 100%. When detecting the density, the lines are formed at a halftone density. In this case, although the scatter-reflected light components oscillate at the period of the line pitch, the oscillation amplitude value is smaller than that at the density of 100%. For example, when the density is 0%, the oscillation amplitude of the scatter-reflected light components is 0. When the density is 100%, the oscillation amplitude equals that in FIG. 8. When the density is the halftone density, an intermediate oscillation amplitude is obtained. That is, when the plurality of lines are formed under the condition that an almost predetermined amount of scatter-reflected light components is obtained at the density of 100%, an almost predetermined amount of scatter-reflected light components is obtained even at the halftone density.

Figure 9:
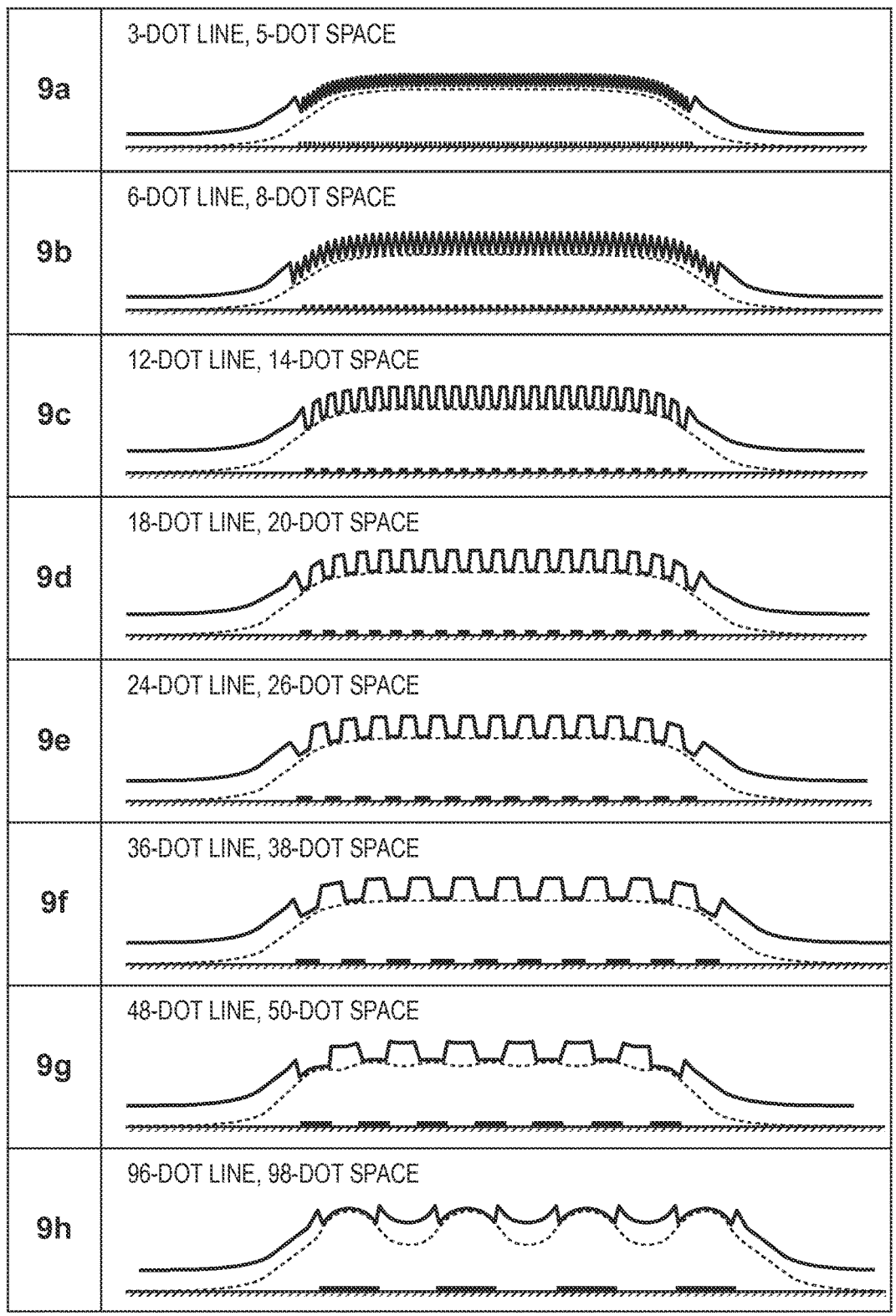
FIG. 9 is a view showing the relationship between the reflected light and the line and space widths of the detection image when the gap distance is 4 mm.

FIG. 9 shows waveforms when, out of the conditions under which the waveforms shown in FIG. 8 are acquired, only the gap distance is changed from 1 mm to 4 mm. When the gap distance is 4 mm, the scatter-reflected light amount can be made even by setting the space width to about 40 dots or less. In FIGS. 8 and 9, the condition to make the variation in the scatter-reflected light components fall within a predetermined amount depends on the gap distance. The longer the gap distance is, the larger the space width to make the scatter-reflected light components even is. However, when the gap distance increases, the signal level of the specular-reflected light considerably lowers.

Note that the optical sensor 27 according to this embodiment includes no converging mechanism of light. For this reason, the optical sensor receives scatter-reflected light at various angles, and has a wide detection range as described above. As described above with reference to FIGS. 6A to 6C and 7A to 7C, this characteristic makes the scatter-reflected light amount larger than the specular-reflected light amount depending on the gap distance and the line width. With this scatter-reflected light detection characteristic, it is possible to create a condition under which an almost predetermined amount of scatter-reflected light components can be obtained from the detection image 40 including a plurality of lines. On the other hand, a conventional optical sensor detects only scatter-reflected light components at several angles. Hence, the scatter-reflected light amount is about several % of the specular-reflected light amount. With the scatter-reflected light detection characteristic, the conventional optical sensor cannot obtain the same result as described above even when the scatter-reflected light components are removed by the same method because the scatter-reflected light is not even. When the line pitch of the detection image 40 is narrowed until the detected scatter-reflected light becomes even, the specular-reflected light components also become even on the detection signal.

A method of extracting the specular-reflected light components by removing the scatter-reflected light components by toner for the total light-receiving amount detected by the optical sensor 27 will be described next with reference to FIGS. 10, 11A to 11C, and 12A and 12B. As shown in FIG. 10, the light-receiving element 277 of the optical sensor 27 outputs a current corresponding to the total light-receiving amount. The processing circuit 275 converts the current corresponding to the total light-receiving amount into a voltage, and outputs it to a signal processing unit 28 of the engine control unit 25 as a photodetection signal. The signal processing unit 28 includes a scattered light removing unit 30 that removes scatter-reflected light components from the photodetection signal representing the total light-receiving amount.

A sampling unit 31 in the scattered light removing unit 30 samples the photodetection signal. Each of moving average processing units 32 and 33 calculates the moving average value in a section of the sampled photodetection signal. A differential processing unit 34 performs a differential operation of the moving average values calculated by the moving average processing units 32 and 33, thereby generating a scattered light removed signal in which the scatter-reflected light components cancel each other so as to be removed or suppressed. Note that the interval between the sections in which the moving average processing units 32 and 33 calculate the moving average values is set to a predetermined period according to the pitch of the lines of the detection image 40. For example, the section interval can be set to a period different from the period of oscillation caused by the specular-reflected light components of the photodetection signal described with reference to FIGS. 8 and 9. More specifically, for example, the interval between the two sections can be set such that the moving average processing unit 33 obtains the moving average in a section including the minimum value of the total light-receiving amount shown in FIGS. 8 and 9 while the moving average processing unit 32 obtains the moving average in a section including the maximum value of the total light-receiving amount shown in FIGS. 8 and 9.

Note that although the arrangement shown in FIG. 10 obtains the difference between the moving averages in the two sections, the difference between the sum of the moving averages in a plurality of first sections and the sum of the moving averages in a plurality of second sections can be obtained. For example, the intervals between a total of six sections can be set such that the moving average in each of three second sections including different minimum values of the total light-receiving amount is obtained while the moving average in each of three first sections including different maximum values of the total light-receiving amount shown in FIGS. 8 and 9 is obtained. Note that the number of sections, the length of each section, and the intervals between the sections can be set to various values other than those described above. However, a state capable of detecting the contrast generated by the presence/absence or density difference of the detection image 40 formed on the intermediate transfer belt 8 is basically set. In this embodiment, the simplest arrangement in which two sections are set will be exemplified. However, any other number of sections can be set. Alternatively, a form in the differential processing is performed for the amplitude of the photodetection signal itself without obtaining the moving averages may be used. Each signal waveform of the light-receiving amount illustrated in FIGS. 8 and 9 repeats large and small oscillations at a period corresponding to the striped detection image 40. When the first section and the second section are set to almost ½ the signal period, the highest signal level is detected. This is because the largest signal level difference is obtained by a phase relationship of 0° and 180° from the signal, which oscillates at a period of 360°, like a sine wave or a rectangular wave. Note that a signal level difference exists and is usable at any phase relationship except 0° and 360°.

The scattered light removed signal output from the scattered light removing unit 30 is input to an amplitude data generation unit 50 and a timing data generation unit 60. An amplitude detection unit 51 in the amplitude data generation unit 50 detects the amplitude value of the scattered light removed signal. The detected amplitude value of the scattered light removed signal is stored by an amplitude data management unit 52 and managed as data corresponding to the intensity of the reflected light from the detection image 40, for example, density information. A timing detection unit 61 in the timing data generation unit 60 detects the arrival timing of the scattered light removed signal. The detected timing data is position information corresponding to the formation position of the detection image 40, which can be handled as color misalignment information by managing the relative relationship of timing data with respect to the detection image 40 of each color.

Figure 11A:
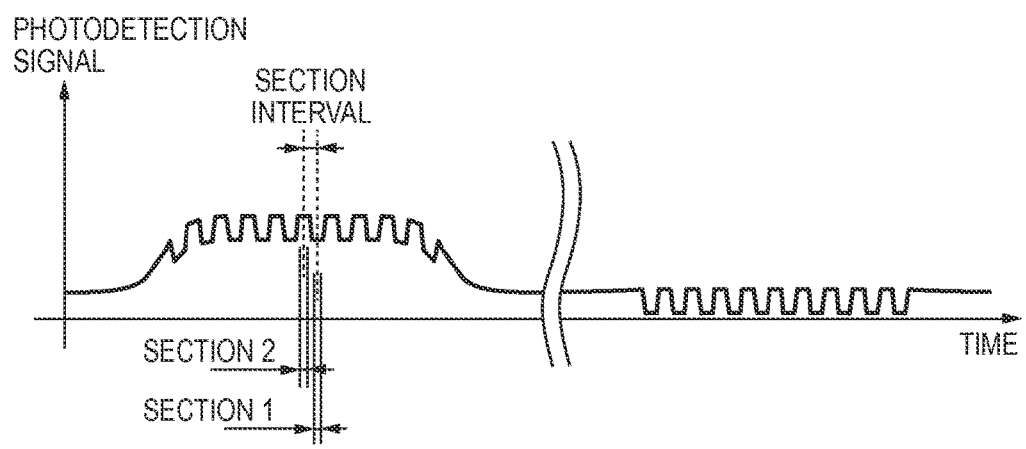
FIGS. 11A to 11C are explanatory views of processing for the detection image including a plurality of lines according to an embodiment.
Figure 11B:
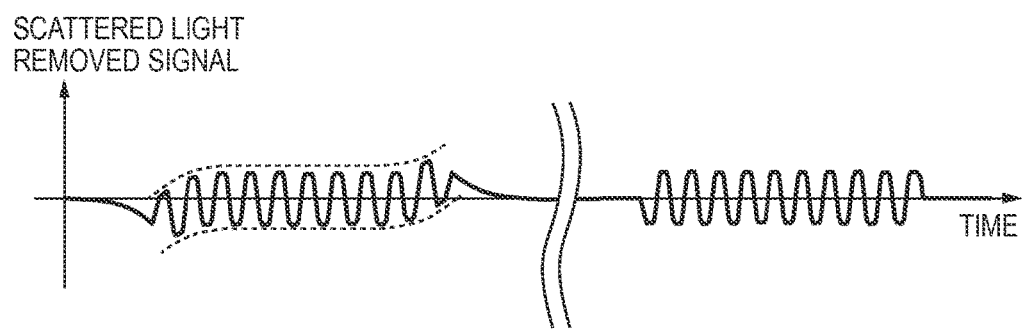
Figure 11C:
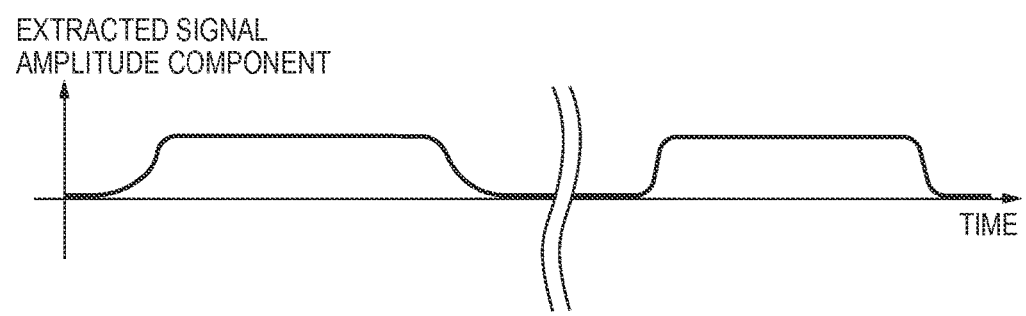

FIG. 11A shows a photodetection signal when the detection image 40 including a plurality of lines is detected. Note that FIGS. 11A to 11C illustrate both waveforms (left side of drawings) upon detecting the detection image 40 formed by toner of a color that generates a large amount of scatter-reflected light and waveforms (right side of drawings) upon detecting the detection image 40 formed by toner of a color that generates a small amount of scatter-reflected light. Note that the line width and the space width of the detection image 40 are set to 36 dots and 38 dots, respectively, and the gap distance is set to 4 mm. That is, the distance between the lines and the gap distance are set such that the oscillation of the scatter-reflected light components in the photodetection signal falls within a predetermined amount. In the toner of the color that generates a large amount of scatter reflection, the whole waveform of the photodetection signal is raised by the influence of the scatter-reflected light, as in FIG. 11A. In the color that generates a small amount of scatter reflection, the irradiation light is absorbed only when the detection image 40 passes, and the signal level attenuates. Section 1 and section 2 in FIG. 11A correspond to the sections to be processed by the moving average processing units 32 and 33, respectively. FIG. 11B shows a signal waveform obtained by performing differential processing of the moving average values in sections 1 and 2. In the signal shown in FIG. 11B, the scatter-reflected light components are removed or reduced. FIG. 11C shows amplitude data extracted from the scattered light removed signal as a waveform. In an image of a halftone density, the amplitude data changes in accordance with the density. As an advantage, it is possible to detect the density of the detection image 40 of each color by the processing independently of the presence/absence of scatter reflection of toner.

Figure 12A:
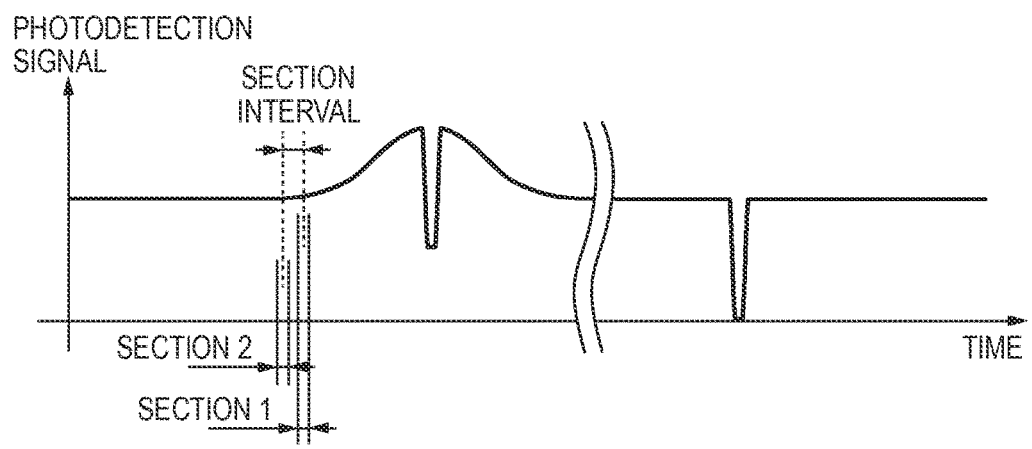
FIGS. 12A and 12B are explanatory views of processing for the detection image including one line according to an embodiment.

FIG. 12A shows a photodetection signal when the detection image 40 including one line is used. Note that FIG. 12A illustrates both waveforms for a color that generates a large amount of scatter reflection and a color that generates a small amount of scatter reflection, like FIG. 11A. The detection image 40 including one line can be used to detect, for example, a color misalignment amount. Note that in FIGS. 12A and 12B, the line width is set to 12 dots, and the gap distance is set to 4 mm.

Figure 12B:
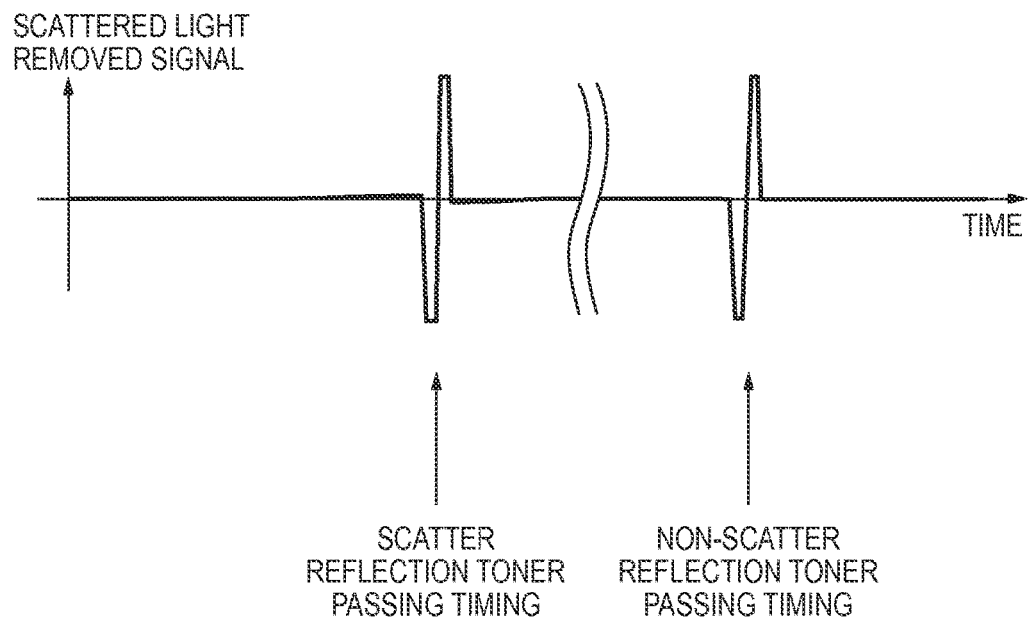

In the toner of the color that causes scatter reflection, the whole waveform is raised by the influence of the scatter-reflected light, as in FIG. 12A. In the toner of the color that causes no scatter reflection, the specular-reflected light is absorbed only when the detection image 40 passes, and the signal level attenuates. Section 1 and section 2 in FIG. 12A correspond to the sections to be processed by the moving average processing units 32 and 33, respectively. FIG. 12B shows a signal waveform obtained by performing differential processing of the moving average values in sections 1 and 2. In the signal shown in FIG. 12B, the scatter-reflected light components are almost removed, and correction to almost the same waveform signal level is performed regardless of the amount of scatter reflection of the toner. In FIG. 12A, the detection image 40 including a single line is used, unlike FIG. 11A. Hence, the scatter-reflected light components are not even before and after the passage of the detection image 40. For this reason, a small amount of scattered light components remains in the scatter-reflected light removed signal. However, this poses no problem because in color misalignment correction, the object is to detect the passing timing of the detection image 40. In addition, as described with reference to FIGS. 6A to 6C and 7A to 7C, the time-rate change in the scatter-reflected light can be made moderate by the gap distance. It is therefore possible to make the difference in scatter-reflected light between the two sections fall within a predetermined amount by appropriately setting the two sections. Furthermore, to prevent the remaining scatter-reflected light components from being problematic, the line width can be set such that the pass through time period of the detection image becomes much smaller than the detection time period of the scatter-reflected light. When the waveform shown in FIG. 12B is compared with a predetermined threshold, and timing data is generated, the arrival timing of the detection image 40 of each color can be detected. Note that the waveform shown in FIG. 12B can also be used to detect the density.

As described above, the detection image 40 including one or more lines is formed on the intermediate transfer belt 8. Reflected light from the intermediate transfer belt 8 is detected by the optical sensor 27. Differential processing is performed for values of the detected reflected light from one or more positions, thereby removing the scatter-reflected light components by toner from the reflected light. In addition, by using the amplitude value information and timing information of the signal obtained by removing the scatter-reflected light, the density information and color misalignment information of the toner image of each color can be detected. When the density information is fed back to the voltage condition of each bias or a process formation condition such as laser power, the maximum density or halftone characteristic of each color is corrected. In addition, when the print start positions in the main scanning direction and sub-scanning direction and the image clock are adjusted for each color based on the color misalignment information, the color misalignment is corrected. Note that the lines include not only a solid line but also a discontinuous line such as a broken line or a dotted line, as described above. In the above-described embodiment, the line of the detection image 40 is perpendicular to the moving direction of the intermediate transfer belt 8. However, the line may be drawn, for example, obliquely with respect to the perpendicular direction. That is, the detection image 40 need only be an image whose toner amount (developing material amount) periodically changes in the moving direction of the intermediate transfer belt 8, and can include a line in a direction different from the moving direction of the detection image 40.

The optical sensor 27 according to this embodiment includes no converging mechanism of light. For this reason, the optical sensor can be downsized to a fraction of the conventional size, and can generate a signal in which the scattered light component from the detection image 40 is accurately removed. In addition, since no converging mechanism exists, the detection resolution can be increased without posing a problem by variations in the manufacture. Furthermore, since the detection resolution is high, the size of the image used to detect color misalignment or density can be made small.

Note that the optical sensor 27 and the signal processing unit 28 according to this embodiment are advantageous in being able to easily freely set the number of sections to obtain the moving averages, the section length, and the section interval. In this embodiment, differential processing is performed for reflected light at the same angle from the intermediate transfer belt 8 serving as the counter member. Hence, even when the counter member has a curved shape, the necessity of correction processing of the reflected light caused by the curved shape of the counter member hardly occurs. For this reason, there is an advantage in increasing the degree of freedom in arranging the optical sensor 27 in the image forming apparatus. In addition, since the differential processing is performed for sampled and accumulated data, there is an advantage in freely setting the regions of the intermediate transfer belt 8 for which the differential processing is performed independently of the size of the optical sensor 27. It is also easy to set the sampling rate in accordance with the line pitch of the detection image 40.

Second Embodiment

The second embodiment will be described next mainly concerning the difference from the first embodiment. The signal waveforms shown in FIGS. 11A and 12A are obtained when an intermediate transfer belt 8 having a very smooth surface is used. However, many intermediate transfer belts 8 have an uneven surface. This unevenness causes fluctuation (to be referred to as belt surface noise hereinafter) in the photodetection signal. In an optical sensor 27 exemplified in this embodiment, the light-emitting region of a light-emitting element 272 and the light-receiving region of a light-receiving element 277 have sizes of several ten to several hundred μm. For this reason, if unevenness in a size of several ten to several hundred μm exists on the surface of the intermediate transfer belt 8, relatively large belt surface noise is generated. When the belt surface noise is superimposed on the photodetection signal, the detection accuracy may lower. Hence, in density detection or the like in which the detection accuracy is important, an error caused by the influence of the belt surface noise is preferably made as small as possible.

Figure 16A:
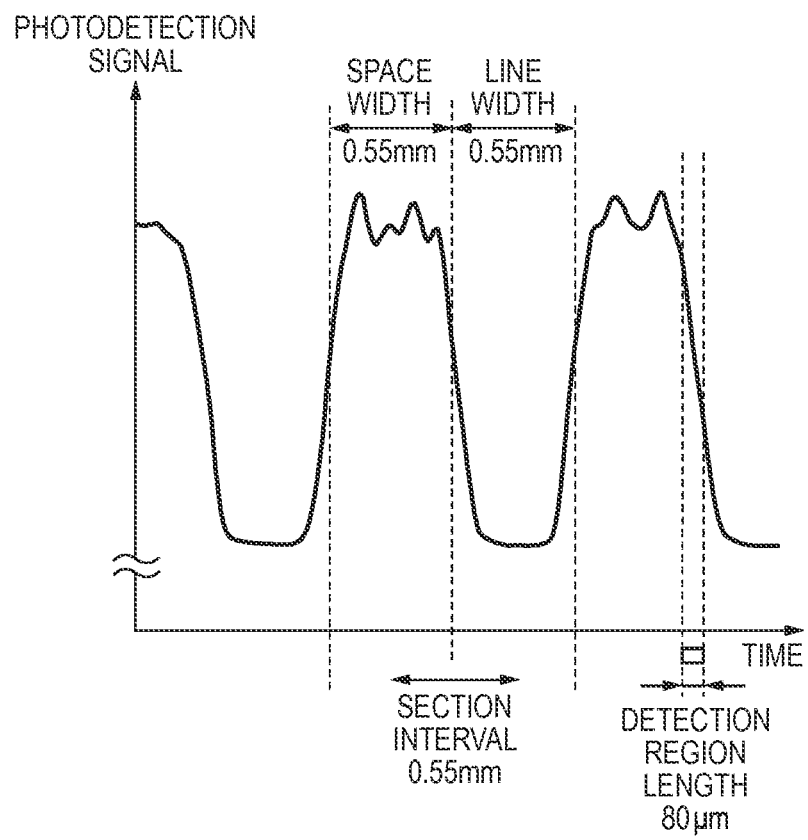
FIGS. 16A and 16B are explanatory views of the relationship between sections and the scattered light removed signal.

FIG. 16A is an enlarged view of the waveform shown in FIG. 11A. Note that a detection image 40 is formed such that the line width and the space width are set to 0.55 mm. The light-receiving region of the light-receiving element 277 has a certain width (length) in the sub-scanning direction. Hence, the light-receiving element 277 simultaneously receives specular-reflected light component from a region on the intermediate transfer belt 8 according to the sub-scanning direction width of the light-receiving region. For this reason, changes in the light-receiving amount of the light-receiving element at the boundary between the line and the space of the detection image 40 are averaged by the sub-scanning direction width of the light-receiving region. Hence, even when the reflection characteristic largely changes at the boundary between the line and the space of the detection image 40, the photodetection signal does not abruptly change, and the slope is moderated by the averaging. That is, the larger the sub-scanning direction width of the light-receiving region is, the more moderate the slopes of the photodetection signal are. Note that in this example, the sub-scanning direction width of the light-receiving region is 160 μm. At this time, the light-receiving element 277 simultaneously receives specular-reflected light component within a range of 80 μm in the sub-scanning direction of the surface of the intermediate transfer belt 8.

Figure 16B:
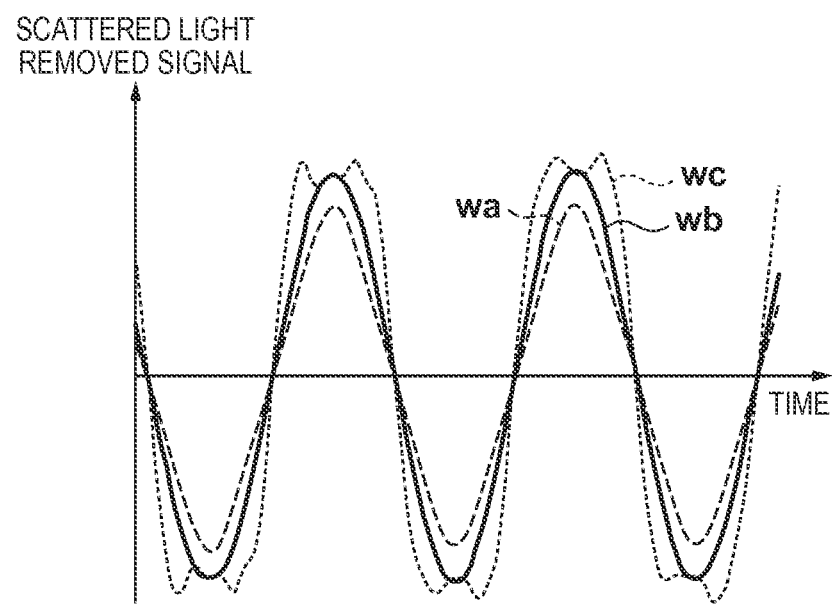

FIG. 16B shows a signal waveform when the section interval between two sections shown in FIG. 11A to 0.55 mm that is ½ the line pitch, and the length of the section, that is, the length of the period to obtain an average value is changed. More specifically, a broken line wa in FIG. 16B indicates a scattered light removed signal when the length of the two sections is set to 0.55 mm that is the same as the line width. Similarly, a solid line wb indicates a waveform when the length of the two sections is set to 0.45 mm that is smaller than the line width by 0.1 mm. Furthermore, a dotted line wc indicates a waveform when the length of the two sections is set to 0.05 mm that is smaller than the line width by 0.5 mm.

The amplitude value of the scattered light removed signal becomes large as the section length shortens, like the solid line wb or the dotted line wc, as compared to the broken line wa with a long section length. However, the waveform of the dotted line wc in which the section length is shortened to 0.05 mm, although the amplitude value is large, relatively large belt surface noise is superimposed at the peak of the amplitude. That is, when the section length is shortened while maintaining the same section interval, the signal amplitude becomes large, and the belt surface noise also becomes large. Defining the signal-to-noise ratio (S/N ratio)=(signal amplitude/belt surface noise), the condition of the section length under which the S/N ratio is optimized will be described below.

Note that in the following description, line width=space width is defined as the reference section length, and the difference between line width/space width and a section length equal to or smaller than line width/space width is defined as the section length decrease amount. FIG. 17A shows the relationship between the section length decrease amount and the signal amplitude value that is the amplitude in one period of the scattered light removed signal. As is apparent from FIG. 17A, the signal amplitude value is minimum when the section length decrease amount is 0 mm, and becomes large when the section length decrease amount is increased. However, the relationship is not a proportional. First, when the section length decrease amount is increased from 0 mm, the signal amplitude steeply becomes large. This is because the length of time of averaging at the rise and fall of the signal shown in FIG. 16A decreases. As shown in FIG. 17A, when the amplitude increases to some extent, the increase amount of the amplitude value then becomes moderate even if the section length decrease amount is increased. When the section length decrease amount is further increased, the amplitude value steeply becomes large due to the influence of belt surface noise superimposed on the signal waveform.

The relationship between the section length decrease amount and the belt surface noise will be described next. FIG. 17B shows the relationship between the section length decrease amount and the noise amplitude value in one period of the scattered light removed signal. When the section length decrease amount is 0.35 mm or more, that is, the section length is 0.2 mm or less, the amplitude value of the belt surface noise steeply increases. This occurs due to the characteristic of the uneven shape of the surface of the intermediate transfer belt 8 used in this measurement. As the result of examination, the noise period by the unevenness of the intermediate transfer belt surface is formed with respect to the section length of about 0.2 mm as the center. For this reason, if the section length is smaller than 0.2 mm, the belt surface noise cannot be averaged, and the noise level steeply rises.

FIG. 17C shows the relationship between the S/N ratio and the section length decrease amount decided by the signal amplitude value shown in FIG. 17A and the noise amplitude value shown in FIG. 17B. In this example, the S/N ratio is maximized when the section length decrease amount is 0.1 mm, that is, the section length is 0.45 mm.

When the measurement was done for a line width and a space width except those in FIG. 16A, the same result as described above was obtained. The section length decrease amount that maximizes the S/N ratio is almost constant independently of the line width or the section interval because the slopes at the rise and fall of the signal waveform hardly change even when the line width is changed. Hence, in the above-described example, when the section length is smaller than the line width of the detection image 40 by 0.1 mm, a high S/N ratio can be ensured.

The noise period of the intermediate transfer belt 8 affecting the S/N ratio changes depending on the material or type of the intermediate transfer belt 8. Hence, the section length decrease amount of 0.1 mm is merely an example, and the optimum section length decrease amount changes depending on the material and surface state of the intermediate transfer belt 8, the size of the light-receiving element 277, and the like.

Note that although the surface of the intermediate transfer belt 8 provided in the image forming apparatus has unevenness of level unrecognizable by a human, unevenness of several hundred μm or more that causes an image distortion recognizable by a human rarely exists because of its application purpose. Noise abruptly increases when the section length becomes almost equal to or less than the level of unevenness. On the other hand, the signal amplitude value shown in FIG. 17A depends on not the surface shape of the intermediate transfer belt 8 but the slope of the signal waveform. It is therefore possible to obtain the highest S/N ratio by setting the section length slightly smaller than the line width independently of the material or surface state of the intermediate transfer belt 8. If a high S/N ratio is obtained, the density detection accuracy can especially be increased.

Obtaining a high S/N ratio is also effective in detecting the position of the detection image 40. FIGS. 18A and 18B show a photodetection signal and a scattered light removed signal obtained by measuring the detection image 40 including one line using the intermediate transfer belt 8 having unevenness of several ten to several hundred μm on the surface, respectively. Note that FIGS. 18A and 18B illustrate a waveform for a color that generates a large amount of scatter-reflected light (left side of drawings) and a waveform for a color that generates a small amount of scatter-reflected light (right side of drawings), like FIGS. 12A and 12B. The position of the detection image 40 can be detected by comparing the scattered light removed signal shown in FIG. 18B with a threshold. FIG. 18B shows a threshold settable range considering the belt surface noise. If the belt surface noise is small, the threshold settable range widens. That is, the higher the S/N ratio is, the wider the threshold settable range is, and the higher the detection error tolerance to irregularly generated noise and the like is.

Note that the influence on the slope of the photodetection signal waveform has been described using an example in which the light-receiving element 277 whose light-receiving region has a sub-scanning direction width of 160 μm is used. When the light-receiving element 277 whose light-receiving region has a sub-scanning direction width smaller than 160 μm is used, the slope of the photodetection signal becomes steeper than in FIG. 16A, and the superimposed belt surface noise becomes large. As a result, the section length decrease amount that maximizes the S/N ratio becomes smaller than that when the sub-scanning direction width of the light-receiving region is 160 μm. The slope of the signal waveform can thus change depending on the sub-scanning direction length of the light-receiving element 277.

However, the slope of the signal waveform can be changed not only by the sub-scanning direction length of the light-receiving region of the light-receiving element 277 but also by processing of the subsequent stage, for example, averaging the photodetection signal or removing noise using a low-pass filter. Hence, even when a light-receiving element having a shorter light-receiving region is used, a signal having the same slope can be generated by processing of the subsequent stage, and a signal having the maximum S/N ratio can be obtained by the same section length decrease amount. That is, the maximum S/N ratio can be obtained by setting an optimum section length decrease amount in accordance with the degree of slope of the signal waveform before differential processing.

Third Embodiment

In the first embodiment, reflected light of divergent beams emitted by a point source is detected using the single light-receiving element. In the third embodiment, a light-receiving element array including a plurality of light-receiving elements (light-receiving units) is used. This embodiment will be described below mainly concerning the difference from the first embodiment.

Figure 14A:
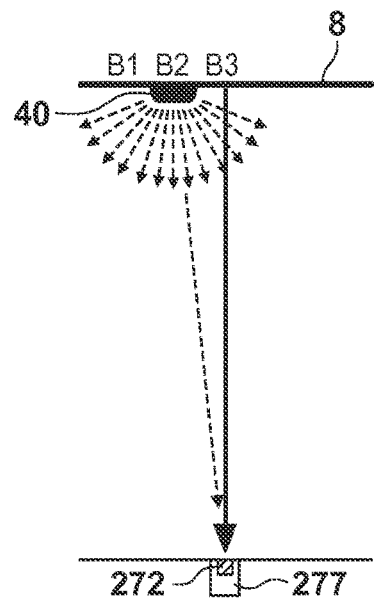
FIGS. 14A to 14E are explanatory views of the difference between the first embodiment and the third embodiment.
Figure 14B:
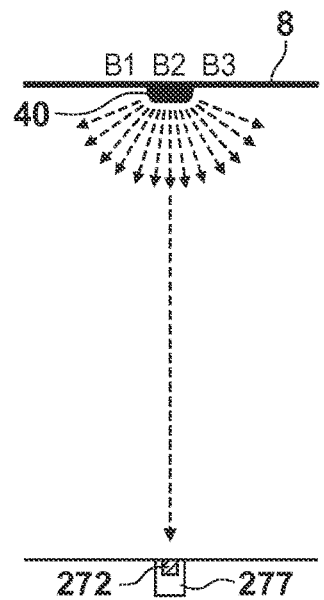
Figure 14C:
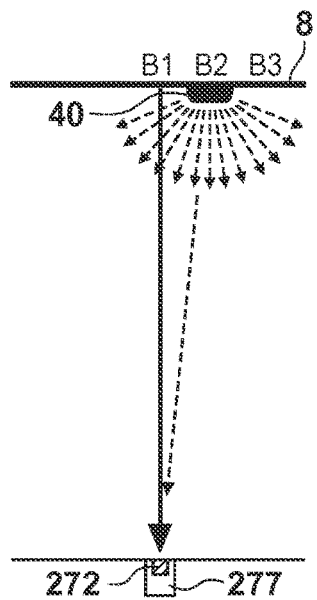

FIGS. 14A to 14C are explanatory views of removal of scatter-reflected light components according to the first embodiment using a single light-receiving element 277. Note that the irradiation light from a light-emitting element 272 is not illustrated to avoid cumbersomeness. FIG. 14A shows a state in which the light-receiving element 277 receives specular-reflected light from a region B3 of an intermediate transfer belt 8. The light-receiving element 277 also receives scatter-reflected light from a line of a detection image 40 in a region B2. FIG. 14B shows a state in which the intermediate transfer belt 8 is then rotated, and the line of the detection image 40 has reached the reflection position of the specular-reflected light to the light-receiving element 277. The light-receiving element 277 hardly receives the specular-reflected light but receives the scatter-reflected light from the line in the region B2. FIG. 14C shows a state in which the intermediate transfer belt 8 is further rotated, and the light-receiving element 277 receives the specular-reflected light from a region B1. The light-receiving element 277 receives the scatter-reflected light from the line in the region B2 as well. That is, the scatter-reflected light is received in all the states of FIGS. 14A to 14C. However, the specular-reflected light is rarely received in the state of FIG. 14B. Hence, a signal in which the scatter-reflected light components are removed can be generated by forming the striped detection image 40 such that the scatter-reflected light becomes even and performing differential processing for values of different positions of the photodetection signal output from the light-receiving element 277.

Figure 14D:
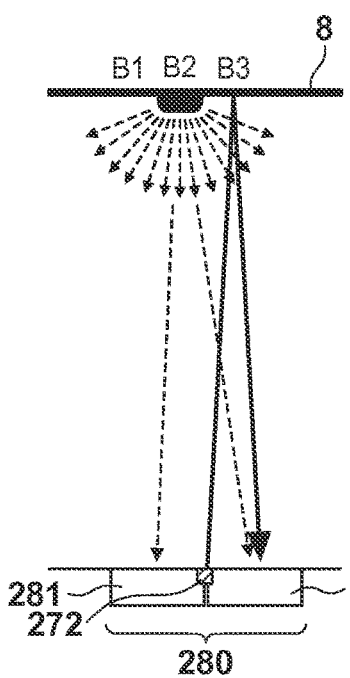
Figure 14E:
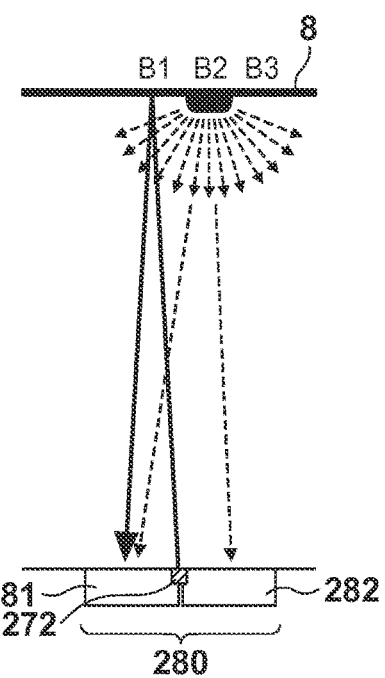

FIGS. 14D and 14E are explanatory views of removal of scatter-reflected light components using a light-receiving element array 280 according to this embodiment. In this embodiment, a simplest case in which two light-receiving elements are used will be explained for the descriptive convenience. However, the number of light-receiving elements may be three or more. Note that the irradiation light from the light-emitting element 272 is partially not illustrated to avoid cumbersomeness. FIG. 14D shows a state in which a light-receiving element 282 receives specular-reflected light from the region B3 of the intermediate transfer belt 8, and another light-receiving element 281 hardly receives the specular-reflected light because of the presence of the line of the detection image 40. FIG. 14E shows a state in which the surface of the intermediate transfer belt 8 has moved, and the line of the detection image 40 has reached the reflection position of the specular-reflected light to the light-receiving element 282. Hence, the light-receiving element 282 hardly receives the specular-reflected light. In the state of FIG. 14E, however, the light-receiving element 281 receives the specular-reflected light from the region B1. Note that as for the scatter-reflected light by the line of the detection image 40, both the light-receiving elements 281 and 282 receive the scatter-reflected light in both the states of FIGS. 14D and 14E. Hence, a signal in which the scatter-reflected light from the detection image 40 is removed can be generated by performing differential processing in real time for values detected by the light-receiving elements 281 and 282 at the same time.

Figure 13:
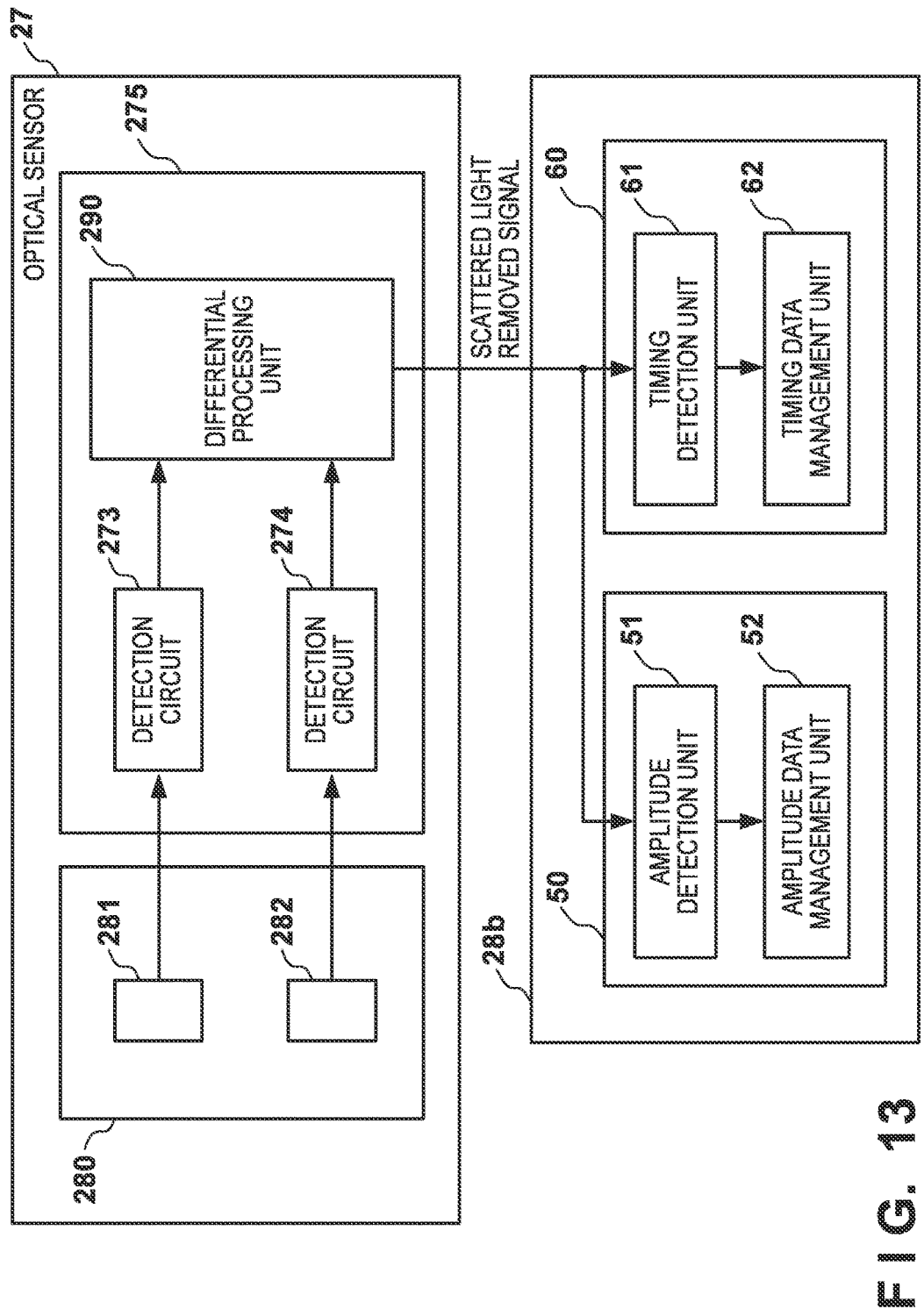
FIG. 13 is a block diagram showing the exemplary arrangement of a detection system according to an embodiment.

As shown in FIG. 13, an optical sensor 27 of this embodiment includes the light-receiving element array 280. The light-receiving element array 280 includes the light-receiving elements 281 and 282. Signals corresponding to the light-receiving amounts output from the light-receiving elements 281 and 282 are converted into photodetection signals by detection circuits 273 and 274 of a processing circuit 275, respectively, and output to a differential processing unit 290. Note that in this embodiment, the light-receiving elements 281 and 282 are single light-receiving elements. However, the sub-scanning direction width of each light-receiving element may further be divided, a plurality of divided small regions of the light-receiving elements 281 and 282 may alternately be arranged, and the sums of values from the alternately arranged small regions may be output to the detection circuits 273 and 274, respectively. That is, first light-receiving elements and second light-receiving elements may alternately be arranged in the sub-scanning direction, and a signal corresponding to the total light-receiving amount of the first light-receiving elements and a signal corresponding to the total light-receiving amount of the second light-receiving elements may be output to the detection circuits 273 and 274, respectively. With this arrangement, position or density information can be detected at a high resolution. The differential processing unit 290 generates a signal in which the scatter-reflected light components are removed by differential processing of the input photodetection signals. In this embodiment, the arrangement distance between the plurality of light-receiving elements is decided by the pitch of the lines of the detection image 40. More specifically, the amount of light received by each of the plurality of first light-receiving elements oscillates as shown in FIG. 11A due to the plurality of lines. The light-receiving elements are arranged at an interval at which the oscillations are in phase. Similarly, the amount of light received by each of the plurality of second light-receiving elements oscillates due to the plurality of lines. The light-receiving elements are arranged at an interval at which the oscillations are in phase. However, the first and second light-receiving elements are arranged so the oscillations of their light-receiving amounts are not in phase, for example, in opposite phases. Note that the number of light-receiving elements, the length of each light-receiving element, and the arrangement distance between the light-receiving elements can variously be set. Basically, values capable of detecting the contrast generated by the presence/absence or density difference of the toner patch 40 formed on the intermediate transfer belt 8 are set.

As in the first embodiment, a signal processing unit 28 detects density and position information for toner of each color using the amplitude value information and timing information of the scattered light removed signal obtained by removing the scatter-reflected light from the toner. In this embodiment, different light-receiving elements simultaneously receive the specular-reflected light components from different sub-scanning direction positions on the detection image 40 and the surface of the intermediate transfer belt 8, and differential processing is performed, thereby detecting density or position information. For this reason, the arrangement related to the signal processing and the like can be simple. Additionally, there is an advantage of monitoring the signal obtained by removing the scatter-reflected light from the detection image 40 in real time.

As in the second embodiment, when the sub-scanning direction width of the light-receiving region of each light-receiving element is made shorter than the width of the specular-reflected light at the position of the light-receiving element, which is reflected in the width equal to the line width of the detection image 40 at the intermediate transfer belt 8, the S/N ratio can be raised. This corresponds to setting the section length in the second embodiment shorter than the line width.

Note that in the first embodiment, differential processing is performed for different time positions of a signal representing the time-rate change in the light-receiving amount detected using one light-receiving element. With this processing, the difference in the reflected light amount including specular-reflected light components from different positions of the detection image 40 and the surface of the intermediate transfer belt 8 around it is obtained when the detection image 40 passes through the irradiation region of the light-emitting element 272. For example, in the first embodiment, assume that differential processing is performed for the value at the first time position of the detection signal and the value at the second time position later than the first time position. Note that in the first time, a position on the detection image 40, which is the reflection position of the specular-reflected light to the light-receiving element 277, is defined as the first position, and in the second time, a position on the detection image 40 or the surface of the intermediate transfer belt 8, which is the reflection position of the specular-reflected light to the light-receiving element 277, is defined as the second position. In this case, the distance between the first position and the second position equals a value obtained by multiplying the moving speed of the surface of the intermediate transfer belt 8 by the difference between the first time and the second time. Hence, performing differential processing for the first time position and the second time position corresponds to performing differential processing for the total light-receiving amount when the light-receiving element 277 receives the specular-reflected light from the first position and the total light-receiving amount when the light-receiving element 277 receives the specular-reflected light from the second position. Note that the reflected light amount including the specular-reflected light components includes not only a state in which strong specular-reflected light is received from the spaces of the detection image 40 or the surface of the intermediate transfer belt 8 but also a state in which the light is scatter-reflected by the lines, and the amount of specular-reflected light components is zero or very small.

In the second embodiment, the values at the first time position and the second time position are used as the average value in the section. This section is made shorter than the time to move the intermediate transfer belt 8 by the line width of the detection image 40. This is equivalent to calculating the average value during a time when specular-reflected light from a region of the intermediate transfer belt 8 shorter than the line width of the detection image 40 is received. That is, the above-described embodiment is equivalent to calculating the difference between the total light-receiving amount during a time when the specular-reflected light from the first region of the detection image 40 is received and the total light-receiving amount during a time when the specular-reflected light from the second region of the detection image 40 and the surface of the intermediate transfer belt 8 around it is received.

In the third embodiment, a plurality of, for example, two light-receiving elements are used, and differential processing is performed for signals representing the time-rate changes in the light-receiving amounts detected by the respective light-receiving elements at the same time position. With this processing, the difference in the reflected light amount including specular-reflected light components from different positions of the detection image 40 and the surface of the intermediate transfer belt 8 before and after it is obtained because the light-receiving elements cannot be arranged at the same position and are arranged at different positions. For example, in the third embodiment, assume that two light-receiving units, that is, a first light-receiving unit and a second light-receiving unit are arranged in the sub-scanning direction, the first light-receiving unit outputs a first detection signal, and the second light-receiving unit outputs a second detection signal. In a first time when the first light-receiving unit receives specular-reflected light from a first position of the detection image 40, a position on the detection image 40 or the surface of the intermediate transfer belt 8, which is the reflection position of the specular-reflected light to the second light-receiving unit, is defined as a second position. In this case, the distance between the first position and the second position is the distance corresponding to the distance between the first light-receiving unit and the second light-receiving unit. For example, when the two light-receiving units are arranged as shown in FIG. 14D, the distance between the first position and the second position is ½ the distance between the first light-receiving unit and the second light-receiving unit. In this case, performing differential processing for the values of the first detection signal and the second detection signal at the first time position corresponds to performing differential processing for the light-receiving amounts when the first light-receiving unit receives the specular-reflected light from the first position, and the second light-receiving unit receives the specular-reflected light from the second position. That is, in the above-described embodiment, the difference in the reflected light amount including specular-reflected light components from different positions of the detection image 40 and the surface of the intermediate transfer belt 8 before and after it is obtained.

Note that since the light-receiving region of the light-receiving element is not a line in the sub scanning direction and has a certain width in the sub-scanning direction as well, the light-receiving element simultaneously receives the specular-reflected light components from the certain sub-scanning direction width of the detection image 40 and the intermediate transfer belt 8. This corresponds to obtaining the average value of the light-receiving amounts in the sub-scanning direction. That is, in the first embodiment, differential processing is performed by obtaining the average values in the sections. The width of each section of the first embodiment corresponds to the sub-scanning direction length of the light-receiving region of the light-receiving element in the third embodiment. The section interval between the two sections for which the differential processing is performed in the first embodiment corresponds to the sub-scanning direction arrangement interval between the two light-receiving elements in the third embodiment.

In the second embodiment, making the section length shorter than the moving time by the line width of the detection image 40 corresponds to making the sub-scanning direction length of the light-receiving region of the light-receiving unit shorter than the sub-scanning direction length of the specular-reflected light at the position of the light-receiving unit, which is reflected at the whole line width. The section interval between the two sections for which the differential processing is performed in the second embodiment corresponds to the arrangement interval between the two light-receiving elements in the sub-scanning direction in the third embodiment. Note that not a form in which one light-receiving unit includes one light-receiving element but a form in which one light-receiving unit includes a plurality of light-receiving elements may be used.

In the above-described embodiments, the differential processing can be regarded as differential processing performed while shifting the phase of the photodetection signal. More specifically, the processing in the first and second embodiments is equivalent to branching one photodetection signal into two signals, delaying one photodetection signal by a predetermined amount, and performing differential processing. The predetermined amount to be delayed equals the section interval in the first and second embodiments. The differential processing can be performed not by simply shifting the phase but by performing moving average processing, as a matter of course. In the third embodiment, differential processing is performed for the photodetection signals from the first and second light-receiving units. Since the first and second light-receiving units are arranged at different positions, the photodetection signals from the first and second light-receiving units are out of phase with each other. In this case, the phase difference corresponds to the distance between the arrangement positions of the first and second light-receiving units.

Note that in the first embodiment, differential processing is performed for different time positions of a signal representing the time-rate change in the light-receiving amount detected using one light-receiving element. Assume that the optical sensor 27 is provided to face not a planar region where the surface of the intermediate transfer belt 8 is flat but a curved region where the surface is curved. In this case, in an arrangement that performs differential processing for the light-receiving amounts of a plurality of light-receiving elements, as in the third embodiment, the distance between the surface of the intermediate transfer belt 8 and each light-receiving element changes for each light-receiving element. Hence, the degree of spread of specular-reflected light on the light-receiving element also changes for each light-receiving element. For this reason, in the arrangement of the third embodiment, the detection accuracy may degrade when the opposite surface is curved, as compared to the case in which the opposite surface is flat. To the contrary, in the first embodiment, since one light-receiving element is only used, the detection accuracy does not degrade even when the opposite surface is curved.

Other Embodiments

Aspects of the present invention can also be realized by a computer of a system or apparatus (or devices such as a CPU or MPU) that reads out and executes a program recorded on a memory device to perform the functions of the above-described embodiments, and by a method, the steps of which are performed by a computer of a system or apparatus by, for example, reading out and executing a program recorded on a memory device to perform the functions of the above-described embodiments. For this purpose, the program is provided to the computer for example via a network or from a recording medium of various types serving as the memory device (for example, computer-readable medium).

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2012-277442, filed on Dec. 19, 2012, and Japanese Patent Application No. 2012-277443, filed on Dec. 19, 2012 which are hereby incorporated by reference herein in their entirety.

The invention claimed is:

1. An image forming apparatus comprising:
an image carrier;
a forming unit configured to form a detection image made of a developing material on the image carrier;
an irradiation unit configured to irradiate the image carrier having the formed detection image with light;
a light-receiving unit configured to receive reflected light of the light irradiated by the irradiation unit and output a detection signal corresponding to a light-receiving amount of the reflected light including a specular-reflected light component; and
a detection unit configured to obtain a difference value between a value of the detection signal corresponding to the light-receiving amount of the reflected light from a first position where the detection image is formed and a value of the detection signal corresponding to the light-receiving amount of the reflected light from a second position different from the first position during a time when the detection image formed on the image carrier passes through an irradiation region of the irradiation unit, and to detect one of position information and density information of the detection image based on the difference value, in which a scatter-reflected light component in the detection signal is suppressed,
wherein an amount of the developing material of the detection image changes in a moving direction of the detection image, and
a distance between the image carrier and the light-receiving unit and the change in the amount of the developing material of the detection image are set such that an oscillation of an amount of scatter-reflected light received from the detection image by the light-receiving unit, which occurs due to a movement of the detection image, is not more than a predetermined amount.

2. The apparatus according to claim 1, wherein the forming unit is further configured to form, on the image carrier, the detection image including a plurality of lines made of the developing material in a direction different from a moving direction of the image carrier, and
a length of a detection region at each of the first position and the second position in the moving direction is shorter than the length of the line in the moving direction.

3. The apparatus according to claim 1, wherein the irradiation unit is further configured to irradiate the image carrier with divergent beams.

4. The apparatus according to claim 1, wherein the reflected light is received by the light-receiving unit without passing through an optical member configured to converge or condense the light.

5. The apparatus according to claim 1, wherein the detection unit is further configured to detect one of the position information and the density information of the detection image by performing differential processing of values of the detection signal corresponding to two time positions far apart by a predetermined period.

6. The apparatus according to claim 1, wherein the detection unit is further configured to detect one of the position information and the density information of the detection image by performing differential processing of average values of the detection signal corresponding to two sections far apart by a predetermined period.

7. The apparatus according to claim 1, wherein the detection unit is further configured to detect one of the position information and the density information of the detection image by performing differential processing of a sum of the values of the detection signal corresponding to a plurality of time positions and a sum of the values of the detection signal corresponding to a plurality of time positions far apart from the plurality of positions by a predetermined period.

8. The apparatus according to claim 1, wherein the detection unit is further configured to detect one of the position information and the density information of the detection image by performing differential processing of a sum of average values of the detection signal corresponding to a plurality of sections and a sum of average values of the detection signals corresponding to a plurality of sections far apart from the plurality of sections by a predetermined period.

9. The apparatus according to claim 5, wherein
the predetermined period is a period different from a period of an oscillation that is caused in the detection signal by the change in the amount of the developing material of the detection image when the detection image moves.

10. The apparatus according to claim 9, wherein the predetermined period is a period substantially ½ the period of the oscillation.

11. The apparatus according to claim 1, wherein the irradiation region of the irradiation unit on the image carrier comprises a curved surface.

12. The apparatus according to claim 1, wherein the light-receiving unit comprises at least one first light-receiving unit and at least one second light-receiving unit, and
the detection unit is further configured to detect one of the position information and the density information of the detection image by performing differential processing of a sum of values of first detection signals output from the at least one first light-receiving unit and a sum of values of second detection signals output from the at least one second light-receiving unit.

13. The apparatus according to claim 12, wherein
an oscillation occurs in the first detection signal and the second detection signal due to the change in the amount of the developing material of the detection image when the detection image moves, and
the first light-receiving unit and the second light-receiving unit are arranged such that phases of the oscillation of the first detection signal and the second detection signal are different.

14. The apparatus according to claim 13, wherein the light-receiving unit comprises a plurality of first light-receiving units and a plurality of second light-receiving units, and
the first light-receiving units and the second light-receiving units are arranged such that first detection signals output from the plurality of first light-receiving units are in phase, and second detection signals output from the plurality of second light-receiving units are in phase.

15. The apparatus according to claim 12, wherein
the oscillation of the amount of the developing material of the detection image changes in the moving direction of the detection image, and
the oscillation of the amount of scatter-reflected light received from the detection image by the first light-receiving unit and the second light-receiving unit is not more than the predetermined amount.

16. The apparatus according to claim 12, wherein the detection image includes one line in a direction different from the moving direction of the detection image.

17. The apparatus according to claim 1, wherein a position of an image to be formed is corrected using the position information, or a density of the image to be formed is corrected using the density information.

18. A detection apparatus comprising:
an irradiation unit configured to irradiate an image carrier, on which a detection image made of a developing material is formed, with light;
a light-receiving unit configured to receive reflected light of the light irradiated by the irradiation unit and output a detection signal corresponding to a light-receiving amount of the reflected light including a specular-reflected light component; and
a detection unit configured to obtain a difference value between a value of the detection signal corresponding to the light-receiving amount of the reflected light from a first position where the detection image is formed and the value of the detection signal corresponding to the light-receiving amount of the reflected light from a second position different from the first position, and to detect one of position information and density information of the detection image based on the difference value, in which a scatter-reflected light component in the detection signal is suppressed,
wherein an amount of the developing material of the detection image changes in a moving direction of the detection image, and
a distance between the image carrier and the light-receiving unit and the change in the amount of the developing material of the detection image are set such that an oscillation of an amount of scatter-reflected light received from the detection image by the light-receiving unit, which occurs due to a movement of the detection image, is not more than a predetermined amount.

* * * * *